(12) United States Patent
Sargeant et al.

(10) Patent No.: US 9,833,225 B2
(45) Date of Patent: Dec. 5, 2017

(54) WOUND CLOSURE DEVICE

(75) Inventors: Timothy Sargeant, Guilford, CT (US); Joshua Stopek, Guilford, CT (US); Michael Bettuchi, Middletown, CT (US); Arpan Desai, Hamden, CT (US); Atu Agawu, Princeton, NJ (US); Saumya Banerjee, Hamden, CT (US)

(73) Assignee: Covidien LP, Mansfield, MA (US)

( * ) Notice: Subject to any disclaimer, the term of this patent is extended or adjusted under 35 U.S.C. 154(b) by 1144 days.

(21) Appl. No.: 12/897,011

(22) Filed: Oct. 4, 2010

(65) Prior Publication Data

US 2011/0087272 A1  Apr. 14, 2011

Related U.S. Application Data

(60) Provisional application No. 61/249,627, filed on Oct. 8, 2009.

(51) Int. Cl.
| | |
|---|---|
| *A61B 17/08* | (2006.01) |
| *A61B 17/00* | (2006.01) |
| *A61L 31/04* | (2006.01) |
| *A61L 31/14* | (2006.01) |

(52) U.S. Cl.
CPC .......... *A61B 17/0057* (2013.01); *A61L 31/04* (2013.01); *A61L 31/14* (2013.01); *A61B 2017/0061* (2013.01); *A61B 2017/0065* (2013.01); *A61B 2017/00588* (2013.01); *A61B 2017/00592* (2013.01); *A61B 2017/00597* (2013.01); *A61B 2017/00628* (2013.01); *A61B 2017/00637* (2013.01); *A61B 2017/00641* (2013.01)

(58) Field of Classification Search
CPC ...... A61B 17/0057; A61B 2017/00588; A61B 2017/00592; A61B 2017/00597; A61B 2017/0061; A61B 2017/00628; A61B 2017/00637; A61B 2017/00641
USPC ....... 606/108, 144, 148, 151, 157, 158, 213, 606/215, 216; 604/104, 107, 108, 506, 604/507, 508
See application file for complete search history.

(56) References Cited

U.S. PATENT DOCUMENTS

| | | | |
|---|---|---|---|
| 1,805,319 A * | 5/1931 | Tomkinson | 411/346 |
| 3,272,204 A | 9/1966 | Artandi | |
| 3,874,388 A * | 4/1975 | King et al. | 606/232 |
| 5,116,357 A | 5/1992 | Eberbach | |
| 5,147,374 A | 9/1992 | Fernandez | |
| 5,162,430 A | 11/1992 | Rhee et al. | |
| 5,192,301 A | 3/1993 | Kamiya et al. | |
| 5,306,500 A | 4/1994 | Rhee et al. | |

(Continued)

FOREIGN PATENT DOCUMENTS

| | | |
|---|---|---|
| EP | 2 143 737 A1 | 1/2010 |
| EP | 2 196 193 A1 | 6/2010 |

(Continued)

OTHER PUBLICATIONS

Raul Zurita et al.: "Triclosan Release from Coated Polyglycolide Threads", Macromolecular Bioscience, vol. 6, No. 1, Jan. 5, 2006, pp. 58-69.

(Continued)

*Primary Examiner* — Robert Lynch

(57) ABSTRACT

Biocompatible wound closure devices including an elongate body and a plug member are useful for wound repair.

22 Claims, 7 Drawing Sheets

(56) References Cited

U.S. PATENT DOCUMENTS

| | | | |
|---|---|---|---|
| 5,324,775 A | 6/1994 | Rhee et al. |
| 5,326,350 A | 7/1994 | Li |
| 5,334,216 A | 8/1994 | Vidal et al. |
| 5,370,660 A | 12/1994 | Weinstein et al. |
| 5,394,886 A | 3/1995 | Nabai et al. |
| 5,410,016 A | 4/1995 | Hubbell et al. |
| 5,478,352 A | 12/1995 | Fowler |
| 5,514,181 A | 5/1996 | Light et al. |
| 5,514,379 A | 5/1996 | Weissleder et al. |
| 5,531,759 A | 7/1996 | Kensey et al. |
| 5,543,441 A | 8/1996 | Rhee et al. |
| 5,550,187 A | 8/1996 | Rhee et al. |
| 5,601,602 A | 2/1997 | Fowler |
| 5,630,833 A | 5/1997 | Katsaros et al. |
| 5,752,974 A | 5/1998 | Rhee et al. |
| 5,874,500 A | 2/1999 | Rhee et al. |
| 6,090,996 A | 7/2000 | Li |
| 6,126,675 A | 10/2000 | Shchervinsky et al. |
| 6,152,943 A | 11/2000 | Sawhney |
| 6,165,201 A | 12/2000 | Sawhney et al. |
| 6,179,862 B1 | 1/2001 | Sawhney |
| 6,391,060 B1 | 5/2002 | Ory et al. |
| 6,408,656 B1 | 6/2002 | Ory et al. |
| 6,443,964 B1 | 9/2002 | Ory et al. |
| 6,451,032 B1 | 9/2002 | Ory et al. |
| 6,478,727 B2 | 11/2002 | Scetbon |
| 6,482,179 B1 | 11/2002 | Chu et al. |
| 6,514,534 B1 | 2/2003 | Sawhney |
| 6,566,406 B1 | 5/2003 | Pathak et al. |
| 6,596,002 B2 | 7/2003 | Therin et al. |
| 6,605,294 B2 | 8/2003 | Sawhney |
| 6,656,200 B2 | 12/2003 | Li et al. |
| 6,663,655 B2 | 12/2003 | Ginn et al. |
| 6,673,093 B1 | 1/2004 | Sawhney |
| 6,695,855 B1 | 2/2004 | Gaston |
| 6,703,047 B2 | 3/2004 | Sawhney et al. |
| 6,726,696 B1 | 4/2004 | Houser et al. |
| 6,755,868 B2 | 6/2004 | Rousseau |
| 6,764,500 B1 | 7/2004 | Muijs Van De Moer et al. |
| 6,818,018 B1 | 11/2004 | Sawhney |
| 6,846,319 B2 | 1/2005 | Ginn et al. |
| 6,916,483 B2 | 7/2005 | Ralph |
| 6,964,674 B1 | 11/2005 | Matsuura et al. |
| 6,971,252 B2 | 12/2005 | Therin et al. |
| 7,009,034 B2 | 3/2006 | Pathak et al. |
| 7,021,086 B2 | 4/2006 | Ory et al. |
| 7,025,776 B1 | 4/2006 | Houser et al. |
| 7,101,381 B2 | 9/2006 | Ford |
| 7,328,707 B2 | 2/2008 | Durgin |
| 7,331,199 B2 | 2/2008 | Ory et al. |
| 7,331,981 B2 | 2/2008 | Cates et al. |
| 7,335,220 B2 | 2/2008 | Khosravi et al. |
| 7,338,517 B2 | 3/2008 | Yost et al. |
| 7,347,850 B2 | 3/2008 | Sawhney |
| 7,416,546 B2 | 8/2008 | Pugsley et al. |
| 7,488,340 B2 | 2/2009 | Kauphusman et al. |
| 2001/0046476 A1 | 11/2001 | Plochocka |
| 2002/0049503 A1* | 4/2002 | Milbocker ............ 623/23.72 |
| 2002/0077656 A1 | 6/2002 | Ginn et al. |
| 2002/0077657 A1 | 6/2002 | Ginn et al. |
| 2002/0165581 A1 | 11/2002 | Brucker |
| 2003/0108511 A1 | 6/2003 | Sawhney |
| 2004/0098044 A1 | 5/2004 | Van de Moer |
| 2004/0185250 A1 | 9/2004 | John |
| 2004/0215231 A1 | 10/2004 | Fortune |
| 2005/0043814 A1 | 2/2005 | Kusanagi et al. |
| 2005/0155608 A1 | 7/2005 | Pavcnik et al. |
| 2005/0267528 A1 | 12/2005 | Ginn |
| 2005/0288786 A1* | 12/2005 | Chanduszko ............ 623/11.11 |
| 2006/0015142 A1 | 1/2006 | Malazgirt |
| 2006/0034930 A1 | 2/2006 | Khosravi et al. |
| 2006/0142797 A1 | 6/2006 | Egnelov |
| 2007/0032805 A1 | 2/2007 | Therin et al. |
| 2007/0083268 A1 | 4/2007 | Teoh |
| 2007/0150002 A1 | 6/2007 | Szabo et al. |
| 2007/0170080 A1 | 7/2007 | Stopek et al. |
| 2007/0173844 A1 | 7/2007 | Ralph |
| 2007/0198059 A1 | 8/2007 | Patel et al. |
| 2007/0219583 A1 | 9/2007 | Sing et al. |
| 2007/0276433 A1 | 11/2007 | Huss |
| 2008/0004657 A1 | 1/2008 | Obermiller et al. |
| 2008/0114092 A1 | 5/2008 | Sawhney |
| 2008/0215087 A1 | 9/2008 | Pavcnik et al. |
| 2008/0312683 A1 | 12/2008 | Drasler et al. |
| 2009/0012558 A1 | 1/2009 | Chen et al. |
| 2009/0056722 A1 | 3/2009 | Swann |
| 2009/0069843 A1 | 3/2009 | Agnew |
| 2009/0247651 A1 | 10/2009 | Kapiamba |

FOREIGN PATENT DOCUMENTS

| | | |
|---|---|---|
| EP | 2 233 160 A2 | 9/2010 |
| EP | 2 233 161 A2 | 9/2010 |
| FR | 2839451 A1 | 11/2003 |
| WO | WO 02/24114 A2 | 3/2002 |
| WO | WO 2004/024030 A1 | 3/2004 |
| WO | 2006009925 A2 | 1/2006 |
| WO | WO 2006/009925 A2 | 1/2006 |
| WO | WO 2008/055197 A2 | 5/2008 |

OTHER PUBLICATIONS

European Search Report for EP 07751966 date of completion is Nov. 5, 2012.

European Search Report for EP 10251753.9-1269 date of completion is Jan. 18, 2011 (3 pages).

European Search Report for EP 10251764.6-1269 date of completion is Jan. 6, 2011 (3 pages).

European Search Report for EP 10251757.0-1269 date of completion is Jan. 12, 2011 (3 pages).

European Search Report for EP 10251756.2-1269 date of completion is Jan. 19, 2011 (3 pages).

International Search Report issued in Application EP 11250562.3 dated Dec. 8, 2011.

International Search Report issued in Application EP 11250564.9 dated Dec. 8, 2011.

International Search Report issued in Application EP 11250563.1 dated Dec. 27, 2011.

International Search Report issued in Application EP 11250566.4 dated Dec. 22, 2011.

International Search Report issued in Application EP 11250565.6 dated Dec. 23, 2011.

European Search Report for EP 10251982.4-1269 dated Feb. 24, 2011 (3 pages).

European Search Report for EP 12169360.0-1269 dated Jun. 15, 2012 (6 pages).

International Search Report from application EP 10251719.0 dated May 24, 2013.

* cited by examiner

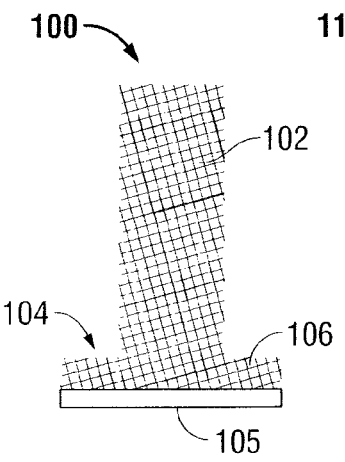
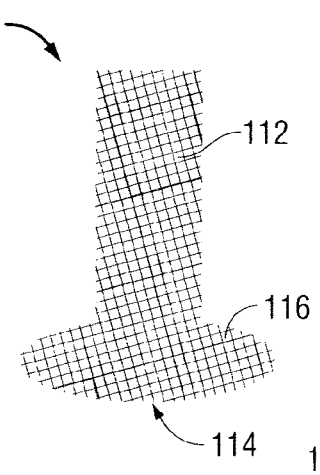
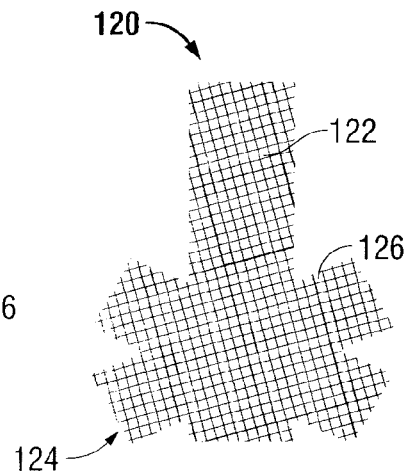
FIG. 10   FIG. 11   FIG. 12
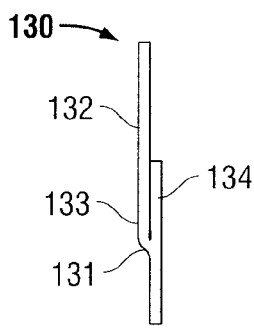
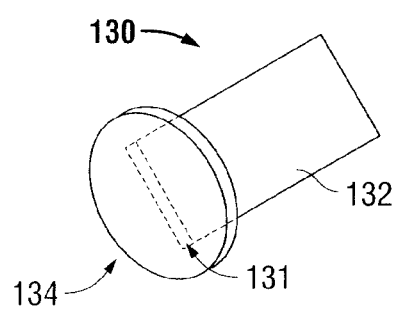
FIG. 13A   FIG. 13B
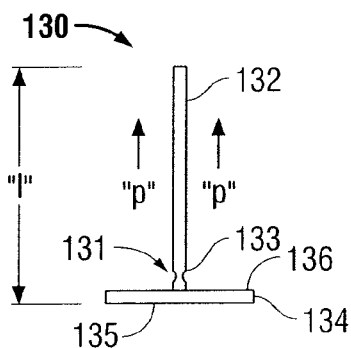
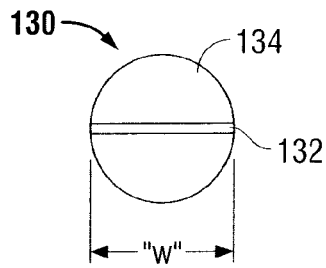
FIG. 13C   FIG. 13D

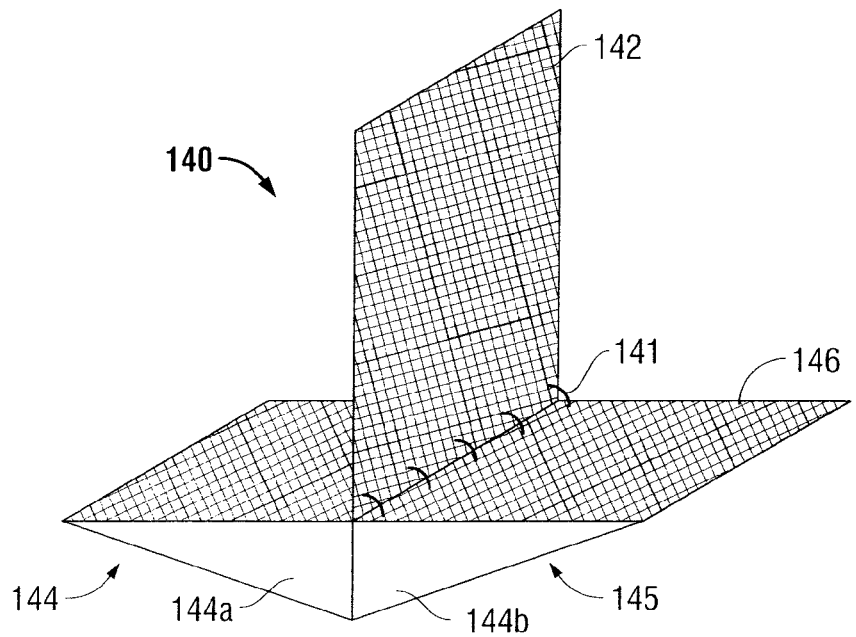
FIG. 14A
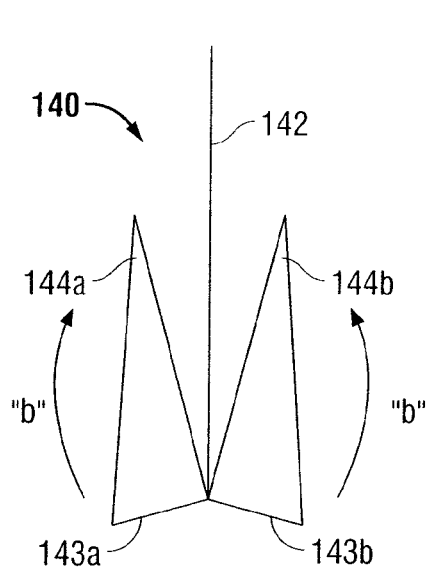 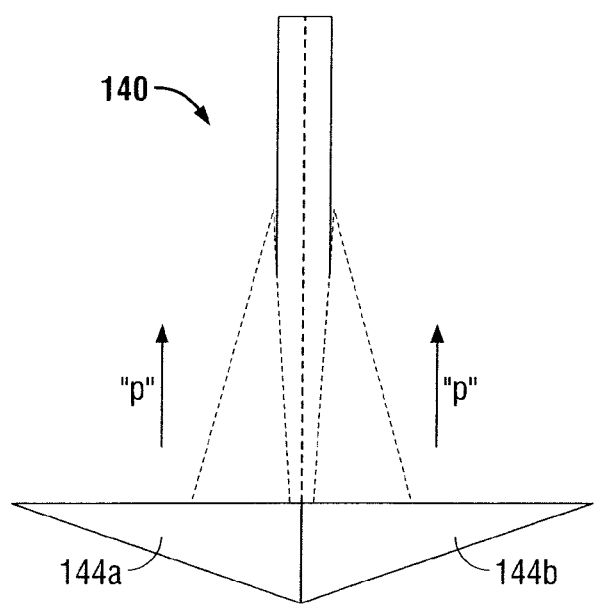
FIG. 14B        FIG. 14C

WOUND CLOSURE DEVICE

CROSS-REFERENCE TO RELATED APPLICATIONS

This application claims the benefit of, and priority to, U.S. Provisional Application No. 61/249,627, filed on Oct. 8, 2009, the entire disclosure of which is incorporated by reference herein.

TECHNICAL FIELD

The present disclosure relates to an implant for providing closure to wounds and, in particular, to a wound closure device for repairing and sealing perforations in tissue, such as laparoscopic port sites.

DESCRIPTION OF THE RELATED ART

A variety of surgical procedures, for example, laparoscopic procedures, are performed through an access port, during which the access device punctures the tissue to provide access to the surgical site.

A hernia is a protrusion of a tissue, structure, or part of an organ through injured muscle tissue or an injured membrane by which the tissue, structure, or organ is normally contained. Trocar site herniation is a potential complication of minimally invasive surgery. Upon removal of a minimally invasive surgical device or the access port, tissues may not properly heal and can present concerns including reherniation. More specifically, omental and intestinal herniation has been reported with larger trocar sites (10 mm).

Currently, wound closure devices, such as sutures, are used to close various layers of tissue post-surgery. Suturing a patient after removal of an access device may be cumbersome, while accumulating additional costs to the patient such as increased time spent in the operating room.

While conventional methods such as suturing exist, improvements in the field are desired.

SUMMARY

The present disclosure provides wound closure devices, methods for making same, and methods for using same. In embodiments, a wound closure device of the present disclosure may include an elongate body having a proximal end and a distal end, and a plug member having a tissue facing surface including a mesh coupled to the distal end of the elongate body, wherein the plug member includes at least one reactive group.

In embodiments, the plug member, the elongate body, or both, may include at least one reactive group that bonds to tissue. The reactive group may also, in embodiments, bond to the plug member, the elongate body, or both. In embodiments, the elongate body, the plug member, or both, may include a hydrogel.

In embodiments, a wound closure device of the present disclosure may include an elongate body having a proximal end and a distal end, and a plug member having a tissue facing surface coupled to the distal end of the elongate body, wherein the elongate body includes a mesh. The mesh may be a substantially flat sheet and may, in embodiments, be biodegradable.

BRIEF DESCRIPTION OF THE DRAWINGS

Various embodiments of the wound closure devices are described herein with reference to the drawings, in which:

FIG. 10 is a perspective view of a wound closure device in accordance with one embodiment of the present disclosure;

FIG. 11 is a perspective view of a wound closure device in accordance with another embodiment of the present disclosure;

FIG. 12 is a perspective view of a wound closure device in accordance with yet another embodiment of the present disclosure;

FIG. 13A is a side view of a wound closure device in a first, folded position, in accordance with an embodiment of the present disclosure;

FIG. 13B is a side perspective view of the wound closure device of FIG. 13A;

FIG. 13C is a side view of the wound closure device of FIG. 13A in a second, expanded position;

FIG. 13D is a top view of the wound closure device of FIG. 13C;

FIG. 14A is a perspective view of a wound closure device in a deployed position in accordance with one embodiment of the present disclosure;

FIG. 14B is a side view of the wound closure device of FIG. 14A in a folded position;

FIG. 14C is a side view of the wound closure device of FIG. 14A illustrated in a deployed position and the folded position of FIG. 14B is shown in phantom;

DETAILED DESCRIPTION

Figure 1:
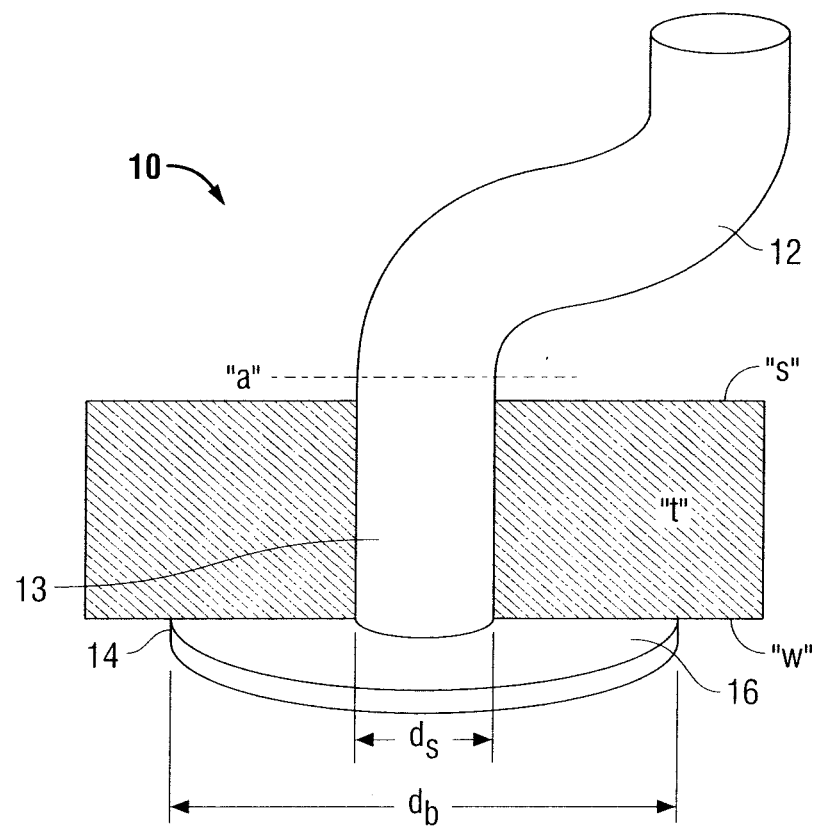
FIG. 1 is a perspective cross-sectional view of a wound closure device in accordance with one embodiment of the present disclosure.

The present wound closure devices facilitate wound closure and may be used to deliver biologics and/or therapeutics to improve healing and reduce scarring, pain, and infection, as well as to provide mechanical stability at the wound site and prevent port site herniation. The wound closure device includes an elongate body for insertion into the perforated tissue of a wound to fill and hold the tissue together, and a plug member attached to a distal end portion of the elongate body, having a substantially flat tissue facing surface for positioning against the internal surface of the tissue to plug or close the wound. In embodiments, the wound closure device is inserted through an insertion device, such as a trocar which, when removed, leaves the wound closure device behind to close the wound.

The components of the wound closure device, i.e., the elongate body and/or plug member, may be fabricated from any biodegradable material that can be used in surgical procedures. The term "biodegradable" as used herein is defined to include both bioabsorbable and bioresorbable materials. By biodegradable, it is meant that the materials decompose, or lose structural integrity under body conditions (e.g., enzymatic degradation or hydrolysis) or are broken down (physically or chemically) under physiologic conditions in the body such that the degradation products are excretable or absorbable by the body. It should be understood that such materials include natural, synthetic, bioabsorbable, and/or non-absorbable materials, as well as combinations thereof, for forming the components of the wound closure device of the present disclosure.

Representative natural biodegradable polymers include: polysaccharides, such as alginate, dextran, chitin, hyaluronic acid, cellulose, collagen, gelatin, fucans, glycosaminoglycans, and chemical derivatives thereof (substitutions and/or additions of chemical groups, for example, alkyl, alkylene, hydroxylations, oxidations, and other modifications routinely made by those skilled in the art); proteins such as albumin, casein, zein, and silk; and copolymers and blends thereof, alone or in combination with synthetic biodegradable polymers.

Synthetically modified natural polymers include cellulose derivatives, such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt. These may be collectively referred to herein, in embodiments, as "celluloses."

Representative synthetic biodegradable polymers include polyhydroxy acids prepared from lactone monomers, such as glycolide, lactide, caprolactone (including $\epsilon$-caprolactone), valerolactone (including $\delta$-valerolactone), as well as carbonates (e.g., trimethylene carbonate, tetramethylene carbonate, and the like), dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include: poly(lactic acid); poly(glycolic acid); poly(trimethylene carbonate); poly(dioxanone); poly(hydroxybutyric acid); poly(hydroxyvaleric acid); poly(lactide-co-($\epsilon$-caprolactone-)); poly(glycolide-co-($\epsilon$-caprolactone)); polycarbonates; poly(pseudo amino acids); poly(amino acids); polyhydroxyalkanoates; polyalkylene oxalates; polyoxaesters; polyanhydrides; polyortho esters; and copolymers, block copolymers, homopolymers, blends, and combinations thereof.

Other non-limiting examples of biodegradable materials from which the wound closure device may be made include: poly(phosphazine), aliphatic polyesters, polyethylene glycols, glycerols, copoly (ether-esters), polyalkylene oxalates, polyamides, poly (iminocarbonates), polyalkylene oxalates, polyoxaesters, polyphosphazenes, and copolymers, block copolymers, homopolymers, blends, and combinations thereof.

Rapidly bioerodible polymers, such as poly(lactide-co-glycolide)s, polyanhydrides, and polyorthoesters, which have carboxylic groups exposed on the external surface as the surface of the polymer erodes, may also be used.

In embodiments, the elongate body, the plug member, or both, or a coating on the elongate body, the plug member, or both, may be formed from a hydrogel. The hydrogel may be formed of any components within the purview of those skilled in the art. In some embodiments, as discussed further below, the hydrogel may be formed of a natural component, such as collagen, gelatin, serum, hyaluronic acid, combinations thereof, and the like. The natural component may degrade or otherwise be released at the site of implantation as any hydrogel utilized as part of the wound closure device degrades. The term "natural component" as used herein includes polymers, compositions of matter, materials, combinations thereof, and the like, which can be found in nature or derived from compositions/organisms found in nature. Natural components also may include compositions which are found in nature but can be synthesized by man, for example, using methods to create natural/synthetic/biologic recombinant materials, as well as methods capable of producing proteins with the same sequences as those found in nature, and/or methods capable of producing materials with the same structure and components as natural materials, such as synthetic hyaluronic acid, which is commercially available, for example, from Sigma Aldrich.

The hydrogels may be formed from a single precursor or multiple precursors. This may occur prior to implantation or at the time of implantation. In either case, the formation of the hydrogel may be accomplished by having a precursor that can be activated at the time of application to create, in embodiments, a hydrogel. Activation can be through a variety of methods including, but not limited to, environmental changes such as pH, ionicity, pressure, temperature, etc. In other embodiments, the components for forming a hydrogel may be contacted outside the body and then introduced into a patient as an implant, such as a pre-formed wound closure device or component thereof.

Where the hydrogel is formed from multiple precursors, for example two precursors, the precursors may be referred to as a first and second hydrogel precursor. The terms "first hydrogel precursor" and "second hydrogel precursor" each mean a polymer, functional polymer, macromolecule, small molecule, or crosslinker that can take part in a reaction to form a network of crosslinked molecules, e.g., a hydrogel.

In embodiments, the precursor utilized to form the hydrogel may be, e.g., a monomer or a macromer. One type of precursor may have a functional group that is an electrophile or nucleophile. Electrophiles react with nucleophiles to form covalent bonds. Covalent crosslinks or bonds refer to chemical groups formed by reaction of functional groups on different polymers that serve to covalently bind the different polymers to each other. In certain embodiments, a first set of electrophilic functional groups on a first precursor may react with a second set of nucleophilic functional groups on a second precursor. When the precursors are mixed in an environment that permits a reaction (e.g., as relating to pH, temperature, ionicity, and/or solvent), the functional groups react with each other to form covalent bonds. The precursors become crosslinked when at least some of the precursors can react with more than one other precursor. For instance, a precursor with two functional groups of a first type may be reacted with a crosslinking precursor that has at least three functional groups of a second type capable of reacting with the first type of functional groups.

The term "functional group" as used herein refers to groups capable of reacting with each other to form a bond. In embodiments, such groups may be electrophilic or nucleophilic. Electrophilic functional groups include, for example, N-hydroxysuccinimides, sulfosuccinimides, carbonyldiimidazole, sulfonyl chloride, aryl halides, sulfosuccinimidyl esters, N-hydroxysuccinimidyl esters, succinimidyl esters, epoxides, aldehydes, maleimides, imidoesters and the like. In embodiments, the electrophilic functional group is a succinimidyl ester.

The first and second hydrogel precursors may have biologically inert and water soluble cores. More specifically, the electrophilic hydrogel precursors may have biologically inert and water soluble cores, as well as non-water soluble cores. When the core is a polymeric region that is water soluble, suitable polymers that may be used include: polyethers, for example, polyalkylene oxides such as polyethylene glycol("PEG"), polyethylene oxide ("PEO"), polyethylene oxide-co-polypropylene oxide ("PPO"), co-polyethylene oxide block or random copolymers, and polyvinyl alcohol ("PVA"); poly(vinyl pyrrolidinone) ("PVP"); poly (amino acids); poly(saccharides), such as dextran, chitosan, alginates, carboxymethylcellulose, oxidized cellulose, hydroxyethylcellulose, hydroxymethylcellulose, and hyaluronic acid; and proteins, such as albumin, collagen, casein, and gelatin. Other suitable hydrogels may include components such as methacrylic acid, acrylamides, methyl methacrylate, hydroxyethyl methacrylate, combinations thereof, and the like. In embodiments, combinations of the foregoing polymers and components may be utilized.

The polyethers, and more particularly poly(oxyalkylenes) or polyethylene glycol, may be utilized in some embodiments. When the core is small in molecular nature, any of a variety of hydrophilic functionalities can be used to make the first and second hydrogel precursors water soluble. For example, functional groups like hydroxyl, amine, sulfonate and carboxylate, which are water soluble, may be used to make the precursor water soluble. For example, the n-hydroxysuccinimide ("NHS") ester of subaric acid is insoluble in water, but by adding a sulfonate group to the succinimide ring, the NHS ester of subaric acid may be made water soluble, without affecting its reactivity towards amine groups. In embodiments, the precursor having electrophilic functional groups may be a PEG ester.

As noted above, each of the first and second hydrogel precursors may be multifunctional, meaning that they may include two or more electrophilic or nucleophilic functional groups, such that, for example, a nucleophilic functional group on the first hydrogel precursor may react with an electrophilic functional group on the second hydrogel precursor to form a covalent bond. At least one of the first or second hydrogel precursors includes more than two functional groups, so that, as a result of electrophilic-nucleophilic reactions, the precursors combine to form cross-linked polymeric products, in embodiments, hydrogels.

A macromolecule having the electrophilic functional group may be multi-armed. For example, the macromolecule may be a multi-armed PEG having four, six, eight, or more arms extending from a core. The core may be the same or different from the macromolecule forming the arms. For example, the core may be PEG and the multiple aims may also be PEG. In embodiments, the core may be a natural polymer.

The molecular weight (MW) of the electrophilic crosslinker may be from about 2,000 g/mol to about 100,000 g/mol; in embodiments from about 10,000 g/mol to about 40,000 g/mol. Multi-arm precursors may have a molecular weight that varies depending on the number of arms. For example, an arm having a 1000 g/mol of PEG has enough $CH_2CH_2O$ groups to total at least 1000 g/mol. The combined molecular weight of an individual arm may be from about 250 g/mol to about 5,000 g/mol; in embodiments from about 1,000 g/mol to about 3,000 g/mol; in embodiments from about 1,250 g/mol to about 2,500 g/mol. In embodiments, the electrophilic crosslinker may be a multi-arm PEG functionalized with multiple NHS groups having, for example, four, six or eight arms and a molecular weight from about 5,000 g/mol to about 25,000 g/mol. Other examples of suitable precursors are described in U.S. Pat. Nos. 6,152,943; 6,165,201; 6,179,862; 6,514,534; 6,566,406; 6,605,294; 6,673,093; 6,703,047; 6,818,018; 7,009,034; and 7,347,850, the entire disclosures of each of which are incorporated herein by reference. It should be understood that 1 g/mol is equivalent to 1 Dalton and the terms may be used interchangeably herein when referring to molecular weight.

The electrophilic precursor may be a cross-linker that provides an electrophilic functional group capable of bonding with nucleophiles on another component, such as, in certain embodiments, a natural component containing primary amines. The natural component may be endogenous (to the patient, i.e., collagen) to which the electrophilic crosslinker is applied.

In embodiments, one of the precursors may be a nucleophilic precursor possessing nucleophilic groups. Nucleophilic groups which may be present include, for example, $-NH_2$, $-SH$, $-OH$, $-PH_2$, and $-CO-NH-NH_2$. Any monomer, macromer, polymer, or core described above as suitable for use in forming the electrophilic precursor may be functionalized with nucleophilic groups to form a nucleophilic precursor. In other embodiments, a natural component possessing nucleophilic groups, such as those listed above, may be utilized as the nucleophilic precursor.

The natural component may be, for example, collagen, gelatin, blood (including serum, which may be whole serum or extracts therefrom), hyaluronic acid, proteins, albumin, other serum proteins, serum concentrates, platelet rich plasma (prp), combinations thereof, and the like. Additional suitable natural components which may be utilized or added to another natural component include, for example, stem cells, DNA, RNA, enzymes, growth factors, peptides, polypeptides, antibodies, other nitrogenous natural molecules, combinations thereof, and the like. Other natural components may include derivatives of the foregoing, for example, modified polysaccharides such as hyaluronic acid or dextran, which may be naturally derived, synthetic, or biologically derived. For example, in some embodiments, the natural component may be aminated hyaluronic acid.

In embodiments, any of the above natural components may be synthetically prepared, e.g., synthetic hyaluronic acid, which may be purchased from Sigma Aldrich, for example. Similarly, in embodiments the natural component could be a natural or synthetic long chain aminated polymer.

The natural component may provide cellular building blocks or cellular nutrients to the tissue that it contacts in situ. For example, serum contains proteins, glucose, clotting factors, mineral ions, and hormones which may be useful in the formation or regeneration of tissue.

In embodiments, the natural component includes whole serum. In some embodiments, the natural component is autologous, i.e., collagen, serum, blood, and the like.

In embodiments, a multifunctional nucleophilic polymer, such as a natural component having multiple amine groups, may be used as a first hydrogel precursor and a multifunctional electrophilic polymer, such as a multi-arm PEG functionalized with multiple NHS groups, i.e., a PEG ester, may be used as a second hydrogel precursor. In embodiments, the precursors may be in solution(s), which may be combined to permit formation of the hydrogel. Any solutions utilized as part of the in situ forming material system should not contain harmful or toxic solvents. In embodiments, the precursor(s) may be substantially soluble in a solvent such as water to allow application in a physiologically-compatible solution, such as buffered isotonic saline.

In some embodiments, a pre-formed hydrogel may be formed from a combination of collagen and gelatin as the natural component, with a multi-functional PEG utilized as a crosslinker. In embodiments, the collagen and gelatin may be placed in solution, utilizing a suitable solvent. To this solution, hyaluronic acid may be added along with a high pH buffer. Such a buffer may have a pH from about 8 to about 12, in embodiments from about 8.2 to about 9. Examples of such buffers include, but are not limited to, borate buffers, and the like.

In a second solution, an electrophilic crosslinker, in embodiments a multi-arm PEG functionalized with electrophilic groups such as n-hydroxysuccinimide, may be prepared in a buffer such as Hanks Balanced Salt Solution, Dulbecco's Modified Eagle's Medium, Phosphate Buffered Saline, water, phosphate buffer, combinations thereof, and the like. The electrophilic crosslinker, in embodiments, a multi-arm PEG functionalized with n-hydroxysuccinimide groups, may be present in a solution including the above buffer at a concentration from about 0.02 grams/mL to about 0.5 grams/mL, in embodiments, from about 0.05 grams/mL to about 0.3 grams/mL.

The two components may be combined, wherein the electrophilic groups on the multi-arm PEG crosslink the amine nucleophilic components of the collagen and/or gelatin. The ratio of natural component to electrophilic component may be from about 0.01:1 to about 100:1, in embodiments, from about 1:1 to about 10:1.

The nucleophilic component, in certain embodiments, the natural components, e.g., collagen, gelatin, and/or hyaluronic acid, may together be present at a concentration of at least about 1.5 percent by weight of the hydrogel, in embodiments, from about 1.5 percent by weight to about 20 percent by weight of the hydrogel, in other embodiments, from about 2 percent by weight to about 10 percent by weight of the hydrogel. In certain embodiments, collagen may be present from about 0.5 percent to about 7 percent by weight of the hydrogel, in further embodiments, from about 1 percent to about 4 percent by weight of the hydrogel. In another embodiment, gelatin may be present from about 1 percent to about 20 percent by weight of the hydrogel, in further embodiments, from about 2 percent to about 10 percent by weight of the hydrogel. In yet another embodiment, hyaluronic acid and collagen combined as the natural component(s) may be present from about 0.5 percent to about 8 percent by weight of the hydrogel, in further embodiments, from about 1 percent to about 5 percent by weight of the hydrogel. It is also envisioned that the hyaluronic acid may not be present as a "structural" component, but as more of a bioactive agent. For example, hyaluronic acid may be present in solution/gel in concentrations as low as 0.001 percent by weight of the solution/gel and have biologic activity.

The electrophilic crosslinker may be present in amounts of from about 0.5 percent by weight to about 20 percent by weight of the hydrogel, in embodiments, from about 1.5 percent by weight to about 15 percent by weight of the hydrogel.

The hydrogels may be formed either through covalent, ionic or hydrophobic bonds. Physical (non-covalent) crosslinks may result from complexation, hydrogen bonding, desolvation, Van der Waals interactions, ionic bonding, combinations thereof, and the like, and may be initiated by mixing two precursors that are physically separated until combined in situ, or as a consequence of a prevalent condition or change in the physiological environment, including temperature, pressure, pH, ionic strength, combinations thereof, and the like. Thus, the hydrogel may be sensitive to these environmental conditions/changes. Chemical (covalent) crosslinking may be accomplished by any of a number of mechanisms, including: free radical polymerization, condensation polymerization, anionic or cationic polymerization, step growth polymerization, electrophile-nucleophile reactions, combinations thereof, and the like.

In some embodiments, hydrogel systems may include biocompatible multi-precursor systems that spontaneously crosslink when the precursors are mixed, but wherein the two or more precursors are individually stable for the duration of the deposition process. In other embodiments, hydrogels may be formed from a single precursor that crosslinks with endogenous materials and/or tissues.

The crosslinking density of the resulting hydrogel may be controlled by the overall molecular weight of the crosslinker and natural component and the number of functional groups available per molecule. A lower molecular weight between crosslinks, such as 600 daltons (Da), will give much higher crosslinking density as compared to a higher molecular weight, such as 10,000 Da. Elastic gels may be obtained with higher molecular weight natural components with molecular weights of more than 3000 Da.

The crosslinking density may also be controlled by the overall percent solids of the crosslinker and natural component solutions. Increasing the percent solids increases the probability that an electrophilic group will combine with a nucleophilic group prior to inactivation by hydrolysis. Yet another method to control crosslink density is by adjusting the stoichiometry of nucleophilic groups to electrophilic groups. A one to one ratio may lead to the highest crosslink density, however, other ratios of reactive functional groups (e.g., electrophile:nucleophile) are envisioned to suit a desired formulation.

The hydrogel thus produced may be bioabsorbable. For example, hydrogels of the present disclosure may be absorbed from about one day to about 18 months or longer. Absorbable polymers materials include both natural and synthetic polymers, as well as combinations thereof.

In embodiments, one or more precursors having biodegradable linkages present in between functional groups may be included to make the hydrogel biodegradable or absorbable. In some embodiments, these linkages may be, for example, esters, which may be hydrolytically degraded. The use of such linkages is in contrast to protein linkages that may be degraded by proteolytic action. A biodegradable linkage optionally also may form part of a water soluble core of one or more of the precursors. Alternatively, or in addition, functional groups of precursors may be chosen such that the product of the reaction between them results in a biodegradable linkage. For each approach, biodegradable linkages may be chosen such that the resulting biodegradable biocompatible crosslinked polymer degrades or is absorbed in a desired period of time. Generally, biodegradable linkages may be selected that degrade the hydrogel under physiological conditions into non-toxic or low toxicity products.

Biodegradable gels utilized in the present disclosure may degrade due to hydrolysis or enzymatic degradation of the biodegradable region, whether part of the natural component or introduced into a synthetic electrophilic crosslinker. The degradation of gels containing synthetic peptide sequences will depend on the specific enzyme and its concentration. In some cases, a specific enzyme may be added during the crosslinking reaction to accelerate the degradation process. In the absence of any degradable enzymes, the crosslinked polymer may degrade solely by hydrolysis of the biodegradable segment. In embodiments in which polyglycolate is used as the biodegradable segment, the crosslinked polymer may degrade in from about 1 day to about 30 days depending on the crosslinking density of the network. Similarly, in embodiments in which a polycaprolactone-based crosslinked network is used, degradation may occur over a period of time from about 1 month to about 8 months. The degradation time generally varies according to the type of degradable segment used, in the following order: polyglycolate<polylactate<polytrimethylene carbonate<polycaprolactone. Thus, it is possible to construct a hydrogel with a desired degradation profile, from a few days to months, using a different degradable segments.

Where utilized, the hydrophobicity generated by biodegradable blocks such as oligohydroxy acid blocks or the hydrophobicity of PPO blocks in PLURONIC™ or TETRONIC™ polymers utilized to form the electrophilic precursor may be helpful in dissolving small organic drug molecules. Other properties which will be affected by incorporation of biodegradable or hydrophobic blocks include: water absorption, mechanical properties and thermosensitivity.

In other embodiments, the precursors utilized to form the hydrogel may be non-degradable, i.e., they may include any of the macromers, polymers, or cores described above as suitable for use in forming the electrophilic precursor, but possess no ester or other similar degradable linkage. The non-biodegradable linkages may be created through the reaction of an N-hydroxysuccinimidyl carbonate. In one embodiment, the reaction of a multi-arm polyol with a N,N'-dihydroxysuccinimidyl carbonate creates an N-hydroxysuccinimidyl carbonate. The N-hydroxysuccinimidyl carbonate can then be further reacted with a high molecular weight polyamine, such as collagen, aminated hyaluronic acid, gelatin, or dextran, to create the pre-formed hydrogel. High molecular weight polyamines may provide longer implant stability as compared to lower molecular weight polyamines. High molecular weight polyamines may comprise molecular weights from about 15,000 g/mol to about 250,000 g/mol, in certain embodiments, from about 75,000 g/mol to about 150,000 g/mol. It should be understood that when a non-biodegradable linkage is used, the implant is still biodegradable through use of a biodegradable first hydrogel precursor, such as collagen. For example, the collagen may be enzymatically degraded, breaking down the hydrogel, which is then subsequently eroded.

Synthetic materials that are readily sterilized and avoid the dangers of disease transmission involved in the use of natural materials may also be used. Indeed, certain polymerizable hydrogels made using synthetic precursors are within the purview of those skilled in the art, e.g., as used in commercially available products such as FOCALSEAL® (Genzyme, Inc.), COSEAL® (Angiotech Pharmaceuticals), and DURASEAL® (Confluent Surgical, Inc). Other known hydrogels include, for example, those disclosed in U.S. Pat. Nos. 6,656,200; 5,874,500; 5,543,441; 5,514,379; 5,410,016; 5,162,430; 5,324,775; 5,752,974; and 5,550,187.

As noted above, in embodiments, a multi-arm PEG, sometimes referred to herein as a PEG star, may be included to form a hydrogel utilized in forming at least a portion of a wound closure device of the present disclosure. A PEG star may be functionalized so that its arms include biofunctional groups such as amino acids, peptides, antibodies, enzymes, drugs, or other moieties in its cores, its aims, or at the ends of its aims. The biofunctional groups may also be incorporated into the backbone of the PEG, or attached to a reactive group contained within the PEG backbone. The binding can be covalent or non-covalent, including electrostatic, thiol mediated, peptide mediated, or using known reactive chemistries, for example, biotin with avidin.

Amino acids incorporated into a PEG star may be natural or synthetic, and can be used singly or as part of a peptide. Sequences may be utilized for cellular adhesion, cell differentiation, combinations thereof, and the like, and may be useful for binding other biological molecules, such as growth factors, drugs, cytokines, DNA, antibodies, enzymes, combinations thereof, and the like. Such amino acids may be released upon enzymatic degradation of the PEG star.

These PEG stars may also include functional groups as described above to permit their incorporation into a hydrogel. The PEG star may be utilized as the electrophilic crosslinker or, in embodiments, be utilized as a separate component in addition to the electrophilic crosslinker described above. In embodiments, the PEG stars may include electrophilic groups that bind to nucleophilic groups. As noted above, the nucleophilic groups may be part of a natural component utilized to form a hydrogel of the present disclosure.

In some embodiments a biofunctional group may be included in a PEG star by way of a degradable linkage, including an ester linkages formed by the reaction of PEG carboxylic acids or activated PEG carboxylic acids with alcohol groups on a biofunctional group. In this case, the ester groups may hydrolyze under physiological conditions to release the biofunctional group.

The elongate body and/or plug member, and/or a coating on a portion thereof, may thus be a hydrogel formed from one precursor (as by free radical polymerization), two precursors, or made with three or more precursors, with one or more of the precursors participating in crosslinking to form the elongate body and/or plug member, or participating to form a coating or layer over the elongate body and/or plug member.

The elongate body and the plug member can take the form of foams, fibers, filaments, meshes, woven and non-woven webs, porous substrates, compresses, pads, powders, flakes, particles, and combinations thereof as described in the embodiments detailed below. Suitable techniques for forming the components of the wound closure device are within the purview of those skilled in the art and include lyophilization, weaving, solvent evaporation, molding, and the like.

In embodiments, one or both of the elongate body and plug member of the wound closure device of the present disclosure may be in the form of a mesh. Techniques for forming a mesh are within the purview of those skilled in the art and include, for example, casting, molding, needle-punching, hooking, weaving, rolling, pressing, bundling, braiding, spinning, piling, knitting, felting, drawing, splicing, cabling, extruding, and/or combinations thereof. In some embodiments, the mesh may form at least the elongate body and/or plug member. In some embodiments, which will be later described, the mesh may further include reactive groups as described herein. In embodiments, the mesh may be bioabsorbable or non-bioabsorbable.

Where the mesh forms a layer on both the elongate body and the plug member, the mesh itself may act as a living hinge, pivotably connecting the elongate body to the plug member. Filaments utilized to produce the strands of a mesh may have a diameter of from about 1 um to about 2 mm, in embodiments from about 100 um to about 1 mm.

The mesh thus produced may have a thickness of from about 0.2 mm to about 5 mm, in embodiments, from about 1 mm to about 3 mm. The strands may be spaced apart to form pores of from about 100 microns to about 2000 microns in diameter, in embodiments, from about 200 microns to about 1500 microns, in other embodiments, from about 750 microns to about 1250 microns in diameter. Examples of various meshes include those disclosed in U.S. Pat. Nos. 6,596,002; 6,408,656; 7,021,086; 6,971,252; 6,695,855; 6,451,032; 6,443,964; 6,478,727; 6,391,060; and U.S. Patent Application Publication No. 2007/0032805, the entire disclosures of each of which are incorporated by reference herein.

Filaments of the mesh may be monofilament or multi-filament. Where multi-filament constructs are utilized, they may be plaited, braided, weaved, twisted, and the like, or laid parallel to form a unit for further construction into a fabric, textile, patch, mesh, and the like. The distribution of the filaments or strands may be random or oriented.

The mesh may include natural or synthetic, bioabsorbable or non-bioabsorbable materials including those listed herein. Suitable meshes include a collagen composite mesh such as PARIETEX™ (Tyco Healthcare Group LP, d/b/a Covidien, North Haven, Conn.) may be used. PARIETEX™ Composite mesh is a 3-dimensional polyester weave with a resorbable collagen film bonded on one side.

In embodiments, the mesh component may be a substantially flat sheet. In other embodiments, the mesh component may be cylindrical in shape. Cylindrical mesh components may be formed by rolling a flat sheet of mesh to form a hollow cylinder.

In embodiments, where the elongate body is formed of a mesh, the mesh may act as a tissue scaffold, thereby providing a means for tissue integration/ingrowth. Tissue scaffolds also are capable of providing cells with growth and development components. Thus, where the hydrogel of the present disclosure is utilized as a tissue scaffold, it may assist in native tissue regrowth by providing the surrounding tissue with needed nutrients and bioactive agents. In some embodiments, as discussed herein, the hydrogel itself may include a natural component, such as collagen, gelatin, hyaluronic acid, combinations thereof, and the like, and thus the natural component may be released or otherwise degrade at the site of implantation as the tissue scaffold degrades.

A hydrogel utilized to form the elongate body, the plug member, or both, may also function as a tissue scaffold.

The elongate body and plug member of the wound closure device provide wound closure by any of a variety of chemical and/or physical means. The elongate body and/or plug member may include reactive groups on its surface to bind to tissue, or a pre-treated moiety may be applied to the tissue surface that will bond with the device upon implantation.

The reactive groups may be applied to the wound closure device utilizing a variety of means including, but not limited to, spray coating, dip coating, melt pressing, extrusion or co-extrusion, etc. The reactive groups may be in the form of solids, liquids, powders or particulates.

In embodiments, a polymer possessing at least one reactive group is capable of immobilizing the components of the wound closure device to tissue. In other embodiments, the polymer may possess multiple reactive groups. For example, a first reactive group can be used to chemically bond the polymer with the elongate body and/or the plug member and a second reactive group can be used to chemically bond the wound closure device to tissue; the reactive polymer thus forms is a bridge between the elongate body and/or plug member and tissue. Chemical bonding refers to all types of chemical bonding including covalent bonding, crosslinking, ionic bonding, and the like.

In some embodiments, any polymer used to make a component of the wound closure device in accordance with the present disclosure may be functionalized with one or more reactive groups. The polymer may be any suitable biodegradable or non-degradable polymer as described above.

The elongate body and/or plug member may include at least one reactive group for crosslinking the device to the surrounding tissue when placed in situ. As noted above, the resulting reactive device may have single or multi-reactive functionality, or may include a mix of small or oligomeric molecules with reactive moieties capable of covalently bonding with tissue.

In embodiments the reactive device may include cross-linkers, adhesives, sealants, couplers, and the like that are functionalized with at least one free reactive group capable of linking the same to tissue. Additionally, reactive groups may include free functional groups from a precursor utilized to form a hydrogel component of a wound closure device of the present disclosure, as well as any coating thereon.

More specifically, reactive groups include, but are not limited to, isocyanates, N-hydroxy succinimide ("NHS"), cyanoacrylates, aldehydes (e.g., formaldehydes, glutaraldehydes, glyceraldehydes, and dialdehydes), genipin, combinations thereof, as well as other compounds possessing chemistries having some affinity for other components of the composition, tissue, or both. The reactive device may also include any natural or synthetic crosslinkers, including, but not limited to, aldehydes, such as those listed above; lysines, such as trilysine, tetralysine, and/or polylysines; diimides; diisocyanates; cyanamide; carbodiimides; dimethyl adipimidate; starches; and combinations thereof. The reactive components may be monofunctional, difunctional, or multi-functional monomers, dimers, small molecules, or oligomers formed prior to or during implantation.

It is contemplated that a plurality of different reactive groups may be present and that they may be terminally located, or alternatively located along the length of the polymer chain. In embodiments, the polymer has from about 2 to about 50 reactive groups.

In embodiments, the elongate body and/or plug member may include dried components, in embodiments, precursors and/or reactive components as described herein, optionally in particle form. These dry materials may be activated by the presence of aqueous physiological fluids. For example, the precursors and/or reactive components may be applied in a dry form, such as particulate matter or in a solid or semi-solid state, such as a film or foam. In embodiments, at least one of the first or second hydrogel precursors may be provided as a film on a wound closure device of the present disclosure. In some embodiments, these dried precursors may be applied to, or embedded within, a mesh utilized as a component or a portion of a component of a wound closure device of the present disclosure. In embodiments, a first portion of the wound closure device of the present disclosure having a first hydrogel precursor applied thereto is spatially separated from a second portion of the wound closure device having a second hydrogel precursor applied thereto. Having the first and second hydrogel precursors spatially separated from each other prevents them from reacting with each other until the wound closure device is placed at the site of implantation and exposed to the physiological fluids of a patient. In embodiments, this spatial separation of the precursors may occur on the plug member, the elongate body, or both. In other embodiments, this spatial separation may occur for any porous substrate, for example, a mesh, hydrogel, film, foam, combinations thereof, and the like, which may be applied as an outer layer to the elongate body, the plug member, or both.

Alternatively, the first hydrogel precursor(s) and/or reactive components may be applied as a coating to the wound closure device of the present disclosure using any suitable method known to those skilled in the art, including, but not limited to, spraying, dipping, brushing, submersion, vapor deposition, co-extrusion, capillary wicking, film casting, molding, solvent evaporation, and by any other physical contact between the device and the polymer, combinations thereof, and the like.

In embodiments, the first hydrogel precursor(s) and/or reactive components may be incorporated into the wound closure device of the present disclosure prior to forming the wound closure device. In embodiments, the first hydrogel precursor(s) and/or reactive components may be applied to the wound closure device in solution followed by evaporation or lyophilization of the solvent. In embodiments, the first hydrogel precursor(s) and/or reactive components may be applied to the wound closure device as a coating on at least one surface of the wound closure device, or as a film present on at least one surface of the wound closure device.

Where the coating includes dried components, in embodiments, dry precursors, optionally in particle form, upon introduction into a wound, body fluids may provide the necessary moisture to initiate reaction of the precursors and/or reactive components with each other and/or tissue.

Alternatively, the coating may be applied to the device prior to implantation, for example, soaking the medical device in the operating room, prior to implantation. In embodiments, the reactive solution may be contacted with the device by flooding the device with the reactive solution so that an intricate network is formed around the device and/or through the device or portions thereof, optionally bonding with the device. The free reactive groups may then bond to tissue, thereby affixing the device to tissue. For example, in embodiments, a reactive solution may be supplied in a conduit to be used in concert with a specialized injectable package material containing a device. The reactive solution may be injected into the device package any time prior to surgical use. The reactive solution, which may be water soluble or dispersible, may saturate and swell the device in preparation for use. A bioactive agent, described in greater detail below, may also be added either to the reactive solution or directly into the device package at the time of use. Examples of such packaging include those disclosed in U.S. Patent Publication No. 2007/0170080, the entire disclosure of which is incorporated by reference herein.

The second hydrogel precursor likewise may be applied as a coating to the wound closure device using any suitable method within the purview of those skilled in the art including, but not limited to, spraying, brushing, dipping, pouring, laminating, etc. In embodiments, the second hydrogel precursor may be applied as a coating on the wound closure device in any concentration, dimension, and configuration. The coating may form a non-porous layer or a porous layer. In embodiments, the second hydrogel precursor may be applied to the wound closure device as a coating on at least one surface thereof, or in other embodiments, as a film, which may be laminated onto at least one surface thereof.

In embodiments where either the first or second hydrogel precursor forms a non-porous layer, i.e., a film, the thickness of the non-porous layer may be sufficient to allow for only portions of the first hydrogel precursor to react with the second hydrogel precursor before the wound closure device seals a wound. In such embodiments, the remaining unreacted hydrogel precursors may act as a barrier layer between the wound and the surrounding tissue to prevent the formation of adhesions. In forming the hydrogel wound closure device, the precursors may also impart upon the physiological fluids certain properties, such as anti-adhesion. The physiological fluid hydrogel may also act as a barrier layer between the wound and the surrounding tissue to prevent the formation of adhesions. In embodiments, the wound closure device may further contain non-reactive materials that are known to reduce or prevent adhesions, such as hyaluronic acid, PEG and the like. In such embodiments, the non-reactive materials may prevent the formation of adhesions after the first and second hydrogel precursors interact.

Upon introduction into a wound, body fluids may provide the necessary moisture to initiate reaction of the precursors and/or reactive components with each other and/or tissue. In embodiments, this reaction may also result in an uptake of fluids, resulting in a volumetric expansion of the elongate body, the plug member, or both.

Once the components of the wound closure device have reacted, the shape of the device may vary depending upon the condition to be treated. Due to the variability of patient morphology and anatomy, the device may be of any suitable size. In embodiments, the elongate body of the wound closure device may have a length from about 10 mm to about 150 mm and the plug member may have a width from about 5 mm to about 36 mm, in embodiments, the elongate body may have a length from about 30 mm to about 80 mm and the plug member may have a width from about 10 mm to about 15 mm, and in other embodiments, the elongate body may have a length from at least 10 mm and the plug member may have a width from about at least 5 mm. In one particular embodiment, the elongate body may have a width of about 39 mm and a length of about 50 mm.

The wound closure device in accordance with the present disclosure may also be prepared from a polymer having at least one functional group known to have click reactivity, capable of reacting via click chemistry. Click chemistry refers to a collection of reactive groups having a high chemical potential energy capable of producing highly selective, high yield reactions. Examples of click chemistry which may be utilized with a device of the present disclosure include those disclosed in U.S. patent application Ser. No. 12/368,415, the entire disclosure of which is hereby incorporated by reference herein.

The reactive groups react to form extremely reliable molecular connections in most solvents, including physiologic fluids, and often do not interfere with other reagents and reactions. Examples of click chemistry reactions include Huisgen cycloaddition, Diels-Alder reactions, thiol-alkene reactions, and maleimide-thiol reactions. Once fabricated into a desired shape, the wound closure device will have a plurality of functional groups known to have click reactivity at the surface thereof.

Huisgen cycloaddition is the reaction of a dipolarophile with a 1,3-dipolar compound that leads to 5-membered (hetero)cycles. Examples of dipolarophiles are alkenes and alkynes and molecules that possess related heteroatom functional groups (such as carbonyls and nitriles). 1,3-dipolar compounds contain one or more heteroatoms and can be described as having at least one mesomeric structure that represents a charged dipole. They include nitril oxides, azides, and diazoalkanes. Metal catalyzed click chemistry is an extremely efficient variant of the Huisgen 1,3-dipolar cycloaddition reaction between alkyl-aryly-sulfonyl azides, C—N triple bonds, and C—C triple bonds. The results of these reactions are 1,2 oxazoles, 1,2,3 triazoles, or tetrazoles. For example, 1,2,3 triazoles are formed by a copper catalyzed Huisgen reaction between alkynes and alkyl/aryl azides. Metal catalyzed Huisgen reactions proceed at ambient temperature, are not sensitive to solvents, and are highly tolerant of functional groups. Non-metal Huisgen reactions (also referred to as strain promoted cycloaddition) involve use of a substituted cyclooctyne, which possesses ring strain and electron-withdrawing substituents, such as fluorine, that together promote a [3+2] dipolar cycloaddition with azides. These reactions may be well-suited for use herein due to low toxicity as compared to the metal catalyzed reactions. Examples include difluorinated cyclooctynes (DIFO) and azacyclooctynes, such as 6,7-dimethoxyazacyclooct-4-yne (DIMAC). Reaction of the alkynes and azides is very specific and essentially inert against the chemical environment of biological tissues.

The Diels-Alder reaction combines a diene (a molecule with two alternating double bonds) and a dienophile (an alkene) to make rings and bicyclic compounds.

The thiol-alkene (thiol-ene) reaction is a hydrothiolation, i.e., addition of RS-H across a C═C bond. The thiol-ene reaction proceeds via a free-radical chain mechanism. Initiation occurs by radical formation upon UV excitation of a photoinitiator or the thiol itself. Thiol-ene systems form ground state charge transfer complexes and therefore photopolymerize even in the absence of initiators in reasonable polymerization times. However, the addition of UV light increases the speed at which the reaction proceeds. The wavelength of the light can be modulated as needed, depending upon the size and nature of the constituents attached to the thiol or alkene.

Thus, suitable reactive members that may be applied to the polymer include, for example, an amine, sulfate, thiol, hydroxyl, azide, alkyne, alkene, carboxyl groups, aldehyde groups, sulfone groups, vinylsulfone groups, isocyanate groups, acid anhydride groups, epoxide groups, aziridine groups, episulfide groups, and groups such as —$CO_2N$ $(COCH_2)_2$, —$CO_2N(COCH_2)_2$, —$CO_2H$, —CHO, —$CHOCH_2$, —N═C═O, —$SO_2CH$═$CH_2$, —$N(COCH)_2$, and —S—S—$(C_5H_4)N$.

The polymer can be provided with click reactive groups using any variety of suitable chemical processes. For example, the monomers from which the core is made can be functionalized so that the reactive groups appear along the length of the core. In such embodiments, monomers can be initially functionalized with a group such as a halogen to provide a reactive site at which the desired first click reactive group can be attached after polymerization. Thus, for example, a cyclic lactone (e.g., glycolide, lactide, caprolactone, etc.) can be halogenated and then polymerized using known techniques for ring opening polymerization. Once polymerized, the halogenated sites along the resulting polyester chain can be functionalized with the first reactive group. For example, the halogenated polyester can be reacted with sodium azide to provide azide groups along the polymer chain or with propargyl alcohol to provide alkyne groups along the polymer chain. In another example, a propargyl group may be introduced into a cyclic carbonate monomer to form 5-methyl-5-propargyloxycarbonyl-1,3-dioxan-2-one (MPC) which is polymerizable with lactide to form p(LA-co-MPC). Alternatively, the polymer or copolymer backbone may be halogenated. Once halogenated, the backbone can be functionalized with a click reactive functionality by reacting it with a hydroxyacid followed by reaction with sodium azide. The halogen may also be converted directly to the alkyne by reacting it with an alcoholic alkyne such as propargyl alcohol.

Those skilled in the art reading this disclosure will readily envision chemical reactions for activating other materials to render them suitable for use as precursors in the presently described wound closure devices.

In embodiments, polymers possessing reactive groups utilized to form a portion of a wound closure device, or a coating thereon, may be in solution. Suitable solvents for use in forming such a solution include, but are not limited to, saline, water, alcohol, acetone, and combinations thereof.

Methods for forming such solutions are within the purview of those skilled in the art and include, but are not limited to, mixing, blending, sonication, heating, combinations thereof, and the like.

Alternatively, the composition of the present disclosure may be immobilized to the implant through mechanical interactions, such as wicking into pores or capillary action. For example, with woven or knitted implants, such as grafts or meshes, a solution including the composition of the present disclosure may be physically entrapped in pores or between fibers. The implant may be further dried at a specified temperature and humidity level, removing residual solvent and leaving behind a reactive coating, creating a reactive implant.

In embodiments in which a polymer possessing reactive groups is applied to a component of the wound closure device and utilized to adhere the device to tissue, the polymer possessing a reactive group may be applied to a device utilizing any method within the purview of those skilled in the art. For example, the implant may be combined with a composition having at least one free reactive group capable of chemically bonding with living tissue. Chemical bonding with living tissue will immobilize the device to the tissue and reduce the need to utilize other mechanical or physical attachment devices, such as staples, tacks, sutures, and the like to attach the device. The amount of time for the reactive composition to bind to tissue may vary from about 3 seconds to about 20 minutes, in embodiments, from about 10 seconds to about 5 minutes. The amount of time may vary depending upon the concentration of the reactive composition, the use of additives, and the like.

In other embodiments, the composition may crosslink with itself. For example, the reactive groups on a polymer utilized to form a portion of the wound closure device or any coating thereon may self-react around the device, forming an intricate network around and throughout the device, thereby encompassing the device, or portions thereof, without chemically bonding to the device, while maintaining free reactive groups for reacting with tissue.

In some embodiments, a first reactive group in the composition can be used to chemically bond to the device and a second reactive group in the composition can be used to chemically bond the device to tissue. Thus, the composition has more than two reactive groups. More than one reactive group may be free for reacting with tissue; in embodiments, from about 1 reactive group to about 8 reactive groups may be free for reacting with tissue. For example, the reactive composition may react with functional groups in tissue, such as primary amino groups, secondary amino groups, hydroxyl groups, combinations thereof, and the like. In embodiments, the reactive groups may cross-link with collagen in tissue thereby fixing the implant in place. In another example, the reactive component may be reactive to a proteinaceous implant. The chemical reaction between the reactive groups and the device may bind the composition to the device while leaving some reactive groups unreacted for future chemical reactions with a tissue surface in situ.

The reactive composition may be immobilized to a device prior to placement in a patient or, alternatively, may be contacted with the device in situ, thereby anchoring the device to tissue. The device may be supplied as a commercially available implant, such as a mesh, or may be assembled prior to use. As noted above, in embodiments the substrate itself may be made of the reactive precursors. In other embodiments the reactive precursors may form a coating on the implant. The entire surface area, or just a portion of the surface, may have a reactive coating thereon for reacting with tissue. The reactive coating, as noted above, may be applied as a solution. The device may be packaged with the solution, or the solution may be applied to the device prior to application to tissue. In embodiments, the solution may be sprayed, coated, dipped, solvent evaporated, or swabbed onto the device.

Alternatively, adhesion of the elongate body or plug member to the tissue may also be provided by mechanical means, including for example, micro-texture (gecko feet) or barbs. In an embodiment, a knit fabric or mesh may include spiked naps which protrude perpendicularly with respect to the mesh to penetrate and fasten to the device. Examples of such fabrics and textiles include those disclosed in U.S. Pat. No. 7,331,199, the entire disclosure of which is incorporated by reference herein.

Turning now to the figures, embodiments of the wound closure device of the present disclosure are provided. In the description that follows, the term "proximal" as used herein, means the portion of the device which is nearer to the user, while the term "distal" refers to the portion of the device which is further away from the user. The term "tissue" as defined herein means various skin layers, muscles, tendons, ligaments, nerves, fat, fascia, bone, and different organs.

Referring now to FIG. 1, an embodiment of a wound closure device 10 according to the present disclosure is shown. The wound closure device 10 includes an elongate body 12 coupled to a plug member 14. The elongate body 12 is substantially perpendicular to a tissue facing surface 16 of plug member 14. In some embodiments, the elongate body 12 may be integral with the plug member 14, while in other embodiments, the elongate body 12 may be attached or otherwise connected to the plug member 14.

Figure 2:
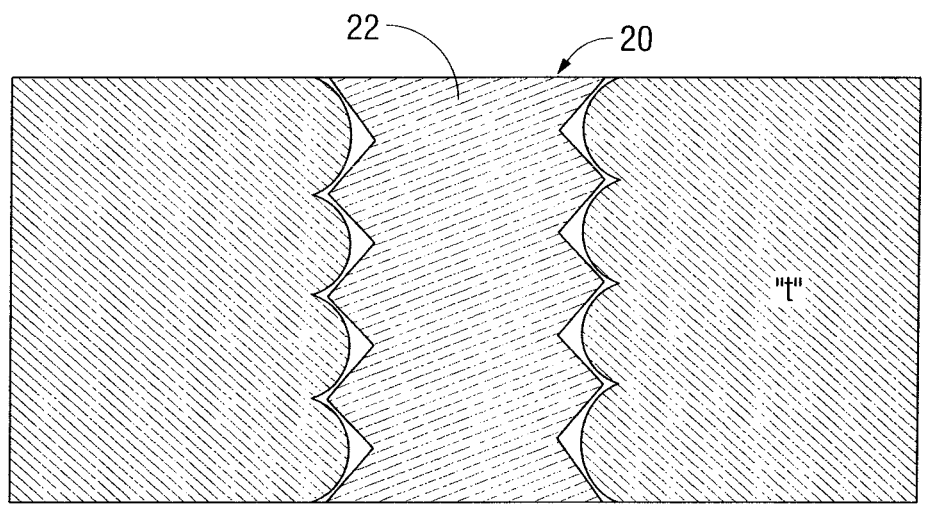
FIG. 2 is a cross-sectional view a wound closure device in accordance with another embodiment of the present disclosure.

The elongate body or stem 12 is adapted to fill or seal the perforation in the tissue "t" and/or bind the perforated tissue together. Accordingly, elongate body 12 may be any shape that fits into the wound. As illustrated in the current embodiment, the elongate body 12 is cylindrical in shape, and elliptical is cross-sectional geometry, but the shape and cross-sectional geometry may also be rectangular, flat, or other shapes within the purview of those skilled in the art and as shown in embodiments disclosed hereafter. For example, as illustrated in FIG. 2, wound closure device 20 is accordion-shaped to allow the elongate body 22 to grow or shrink in length depending on the thickness of tissue "t." Thus, referring again to FIG. 1, the elongate body 12 may be a predefined length which is substantially about the length or depth of the tissue to be sealed, or the elongate body 12 may be made longer to allow for variability in the patient wall thickness. For example, excess length of the elongate body 12 may be trimmed at surface "s" of tissue "t" as indicated by dashed line "a" in FIG. 1.

Plug member or base 14 is adapted to provide closure to the wound by sealing the perforation in the tissue at the inner wall "w" of the tissue "t." The plug member 14 has a tissue facing surface 16 coupled to a distal end 13 of elongate body 12. Plug member 14 may be any shape having a substantially flat, tissue facing surface for abutting the inner wall "w" of the tissue "t," such as a mushroom shape, among others, as envisioned by those skilled in the art. Tissue facing surface 16 defines a diameter "$d_b$" which is larger than the diameter "$d_s$" of the elongate body 12 which is attached thereto for adhering to the inner wall "w" surrounding the perforated tissue "t."

In embodiments, the wound closure device 10 may be a hydrogel or include a hydrogel on at least a portion thereof. For example, the hydrogel could be composed of serum proteins (nucleophilic) crosslinked with succinimidyl ester reactive PEG (electrophilic) to provide the desired adhesion to the tissue and tissue growth.

Upon reacting with amine-containing tissues, the reactive device should fixate to tissue within a useful time range. In alternate embodiments, the reactive groups may be chemically "shielded" or "blocked" in aid of slowing the reaction with tissue, or the reactive groups may simply have slow reaction kinetics.

The amount of time necessary for the reactive component of the composition of the present disclosure to bind the implant to tissue may vary from about 3 seconds to about 20 minutes, in embodiments, about 10 seconds to about 5 minutes.

Figure 3A:
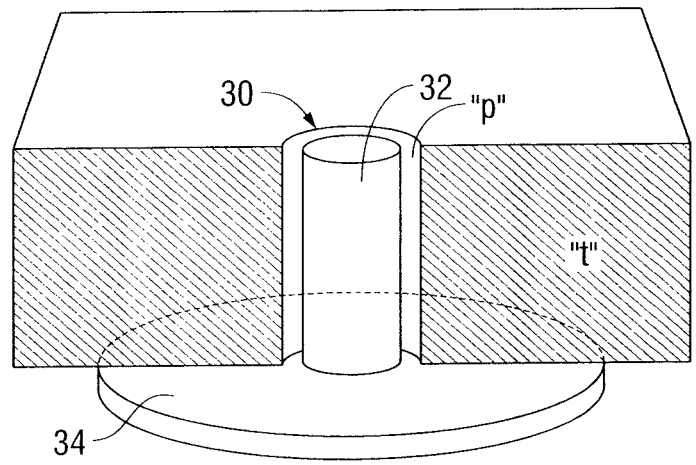
FIG. 3A is a perspective view of a wound closure device having a dehydrated component in accordance with an alternate embodiment of the present disclosure.
Figure 3B:
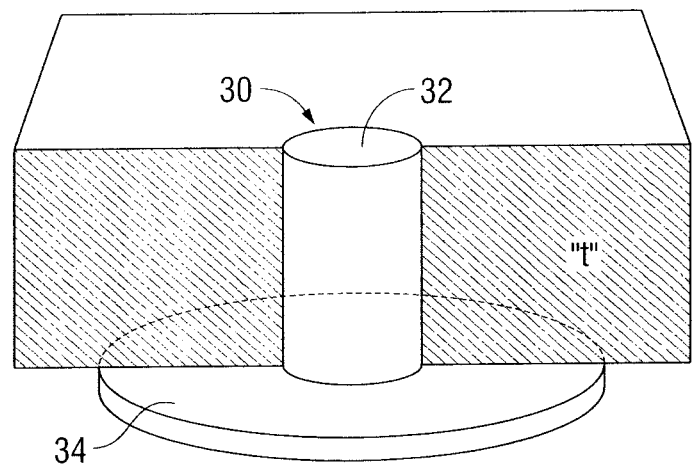
FIG. 3B is a perspective view of the wound closure device of FIG. 3A after rehydration.

At least a portion of the wound closure device may include a polymer foam, as illustrated in FIGS. 3A and 3B. Drying a polymer (such as a hydrogel) to create a foam before placement into tissue may ease the insertion of the device therein and/or may provide control of the size and fit of the device within the tissue. The foam may be created through use of techniques such as lyophilization, particulate leaching, compression molding and others within the purview of those skilled in the art. Various techniques can yield pores of different size and distribution. Varying the pore size and distribution may allow more rapid ingress of water and other aqueous fluids into the foam. Foams may be open-cell or closed-cell foams. It is also possible to affect the rate at which a foam rehydrates in a physiological environment, such as encountered upon implantation in tissue. For example, incorporating a blowing agent during the formation of the foam may lead to more rapid re-hydration due to the enhanced surface area available for the water to diffuse into the foam structure. The hydration of the foam enables the device to become anchored in place to prevent migration and hold the tissue together.

FIG. 3A illustrates a wound closure device 30 having a pre-hydrated foam elongate body 32. Upon placement of the wound closure device 30 into perforation "p" of tissue "t," the elongate body 32 may rapidly rehydrate by irrigating the elongate body 32 with a fluid, such as saline, and/or through contact with the bodily fluids in the physiologic environment. As illustrated in FIG. 3B, the elongate body 32 swells to fill the perforation "p" in the tissue "t." The foam may rehydrate rapidly, in some embodiments, within a few seconds of being placed in a moist tissue environment, or may rehydrate at a slower rate over the course of a few hours. During the hydration process, the foam may expand volumetrically, e.g., in one, two, or three dimensions, to several times its original size, thereby lodging the wound closure device within the tissue and sealing against leakage of fluids through the tissue.

In other embodiments, the wound closure device may include a substantially dehydrated hydrogel, which may, in embodiments, include a foam. The hydrogel component of a device of the present disclosure may swell and/or expand in an amount of from about 5% to about 100% of its original volume, in embodiments, from about 20% to about 80% of its original volume. In embodiments, the swelling of the hydrogel may substantially seal at least one tissue plane.

Figure 4:
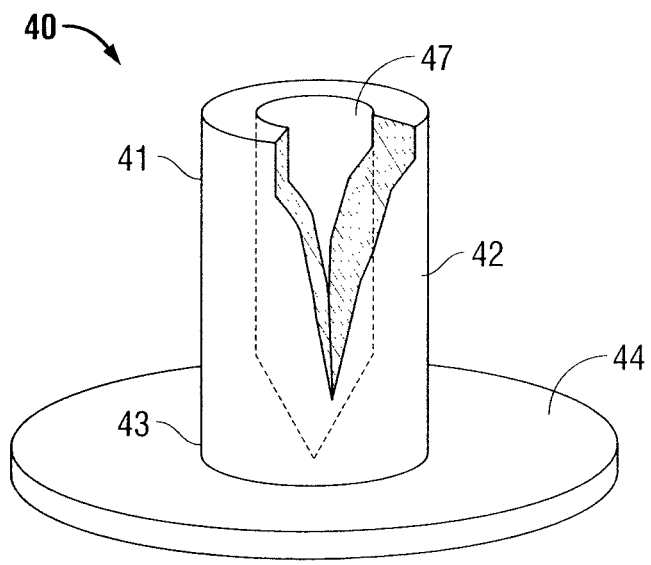
FIG. 4 is a perspective view of a wound closure device in accordance with another embodiment of the present disclosure.

In embodiments, the wound closure device may have an aperture or channel running through a portion thereof to enable volumetric expansion and facilitate hydration of the device. As illustrated in FIG. 4, an aperture 47 is longitudinally disposed within the elongate body 42, extending from the proximal end 41 into the distal end 43. The aperture 47 allows for moisture to reach parts of the elongate body 42, as well as parts of the plug member 44.

Figure 5:
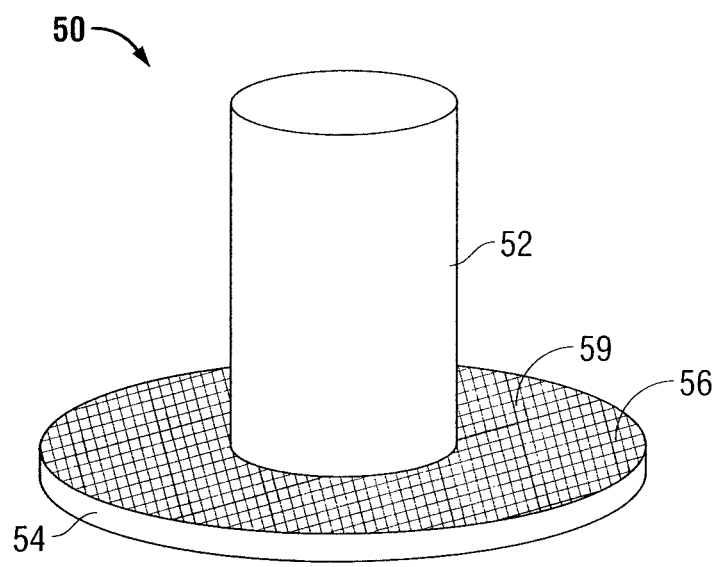
FIG. 5 is a perspective view of a wound closure device in accordance with yet another embodiment of the present disclosure.

Turning now to FIG. 5, a wound closure device 50 may combine a hydrogel with a textile, such as a mesh, to facilitate wound healing. In embodiments, a mesh 59 may be disposed on the tissue facing surface 56 of plug member 54 to aid in tissue adhesion and ingrowth. For example, mesh 59 may be encapsulated or coated with a hydrogel, such as a serum-based hydrogel as described above, and placed on the biodegradable polymer plug member 54, or the mesh 59 may be disposed on at least one surface of the hydrogel plug member 54, as illustrated in FIG. 5. Moreover, mesh 59 may be self-tacking, such as including spiked naps or barbs, to aid the hydrogel in tissue adhesion. In some embodiments, a self-tacking mesh may be utilized without a hydrogel or other adhesive component, which will be later described.

Figure 6:
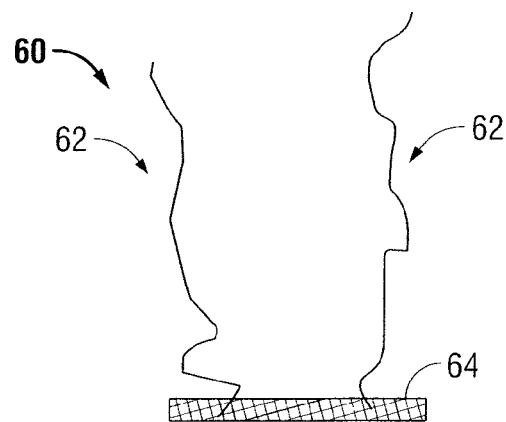
FIG. 6 is a side view of a wound closure device in accordance with another embodiment of the present disclosure.

The elongate body 52 may also be formed from a hydrogel or may be composed of a polymer which is subsequently coated with a hydrogel. It is contemplated that a mesh may also be combined with the elongate body 52 to provide additional tissue adhesion and ingrowth. The elongate body 52 may be provided in a variety of forms to hold the perforated tissue together. For example, as illustrated in FIG. 6, the elongate body of the wound closure device may include sutures 62 which extend from plug member 64 and may be passed through the perforated tissue to hold the tissue together. In embodiments, the sutures may be coated with a polymer possessing at least one reactive group to aid in tissue adhesion. In some embodiments, the sutures may be barbed or have barb-like projections, extending generally outward from the suture body, which assist in tissue retention.

Figure 7:
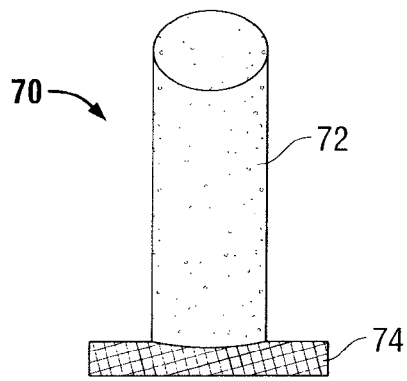
FIG. 7 is a side view of a wound closure device in accordance with yet another embodiment of the present disclosure.
Figure 8:
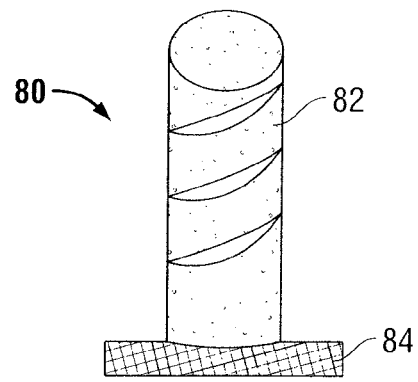
FIG. 8 is a side view of a wound closure device in accordance with one embodiment of the present disclosure.

FIGS. 7 and 8 illustrate wound closure devices 70 and 80, respectively, including an elongate body 72, 82 formed from a hydrogel and a plug member 74, 84 fabricated from a mesh. The plug member 74, 84 may be any of the textile and fabric materials as described herein and may include a coating composition including any of the functional precursor(s) also as described herein. As illustrated in FIG. 8, the elongate body 82 may include a grooved exterior for increased surface area and tissue integration.

Figure 9:
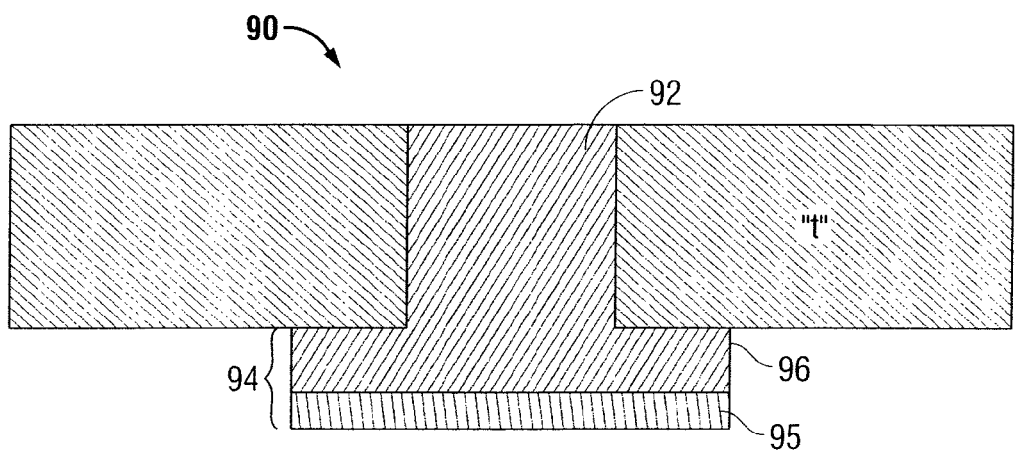
FIG. 9 is a cross-sectional view of an alternate embodiment of a wound closure device in accordance with the present disclosure.

Referring now to FIG. 9, the plug member 94 of the wound closure device 90 may be constructed to include more than one layer, such as a laminate. The tissue facing surface 96 of the plug member 94 may be fabricated from a material having adhesive properties, such as a polymer having reactive groups or a mesh as described above, and the distal surface 95 of the plug member 94 may include a material having anti-adhesive properties, such as a coating of hyaluronic acid or PEG, to prevent adhesion of the device to internal organs. In embodiments, the plug member 94 may be fabricated from a composite material, such as a PARIETEX™ composite mesh, having a porous layer on the tissue facing surface 96 to effect adhesion of the tissue with the plug member 94, and a non-porous layer on the distal surface 95 to prevent adhesion of the plug member 94 with other tissue or organs surrounding the perforated tissue. In other embodiments, the tissue facing surface may include a mesh modified with biodegradable linkers and reactive end groups to bind a second layer, such as a biodegradable collagen film (not shown) on the distal surface of the plug member 94. The distal surface, including the collagen film, may be non-porous to prevent adhesions. Alternatively, the distal surface, including the collagen film, may adhere to the internal organs, and the linkers binding the collagen film to the mesh may degrade in a short period of time thereby separating the two layers and preventing adhesions. In embodiments, both the mesh and the collagen film may be designed to degrade over a longer period of time.

Methods for forming composite meshes are within the purview of those skilled in the art. Multiple layers may be adhered utilizing adhesives, crosslinking of reactive groups on multiple layers, heat molding, co-extrusion, solvent casting, melt pressing, combinations thereof, and the like.

FIG. 10 illustrates an embodiment of a wound closure device 100 including a composite plug member 104 including a mesh on the tissue facing surface 106 and an anti-adhesive distal surface 105. The elongate body 102 includes a mesh which may be utilized alone or in combination with a coating having reactive groups as described herein. In some embodiments, a wound closure device 110 and/or 120 may be solely formed from a mesh, either alone or in combination with a reactive polymer as illustrated in FIGS. 11 and 12. As depicted in FIGS. 11 and 12, wound closure devices 110 and 120, respectively, may include plug members 114 and 124, having tissue facing surfaces 116 and 126, and elongate bodies 112 and 122, all formed of mesh.

FIGS. 13A-13D illustrate a wound closure device 130 including an elongate body 132 and a plug member 134 which are pivotably connected, it being understood that other embodiments described herein may also be pivotably connected. FIGS. 13A and 13B illustrate the wound closure device 130 in a first, collapsed or folded position and FIGS. 13C-13D illustrate the wound closure device 130 in a second, deployed position. The elongate body 132 and the plug member 134 of the wound closure device 130 are coupled via a hinged connection 131. The distal end 133 of the elongate body 132 is hingedly connected to tissue facing surface 136 of the plug member 134 so that the plug member 134 may pivot with respect to the elongate body 132 from the folded position to the deployed position. In certain embodiments, the elongate body 132 and plug member 134 may be hingedly coupled with any of a variety of biodegradable fasteners as envisioned by those skilled in the art. The fasteners may be formed from any of the biodegradable polymers described above, which may be adapted and configured to have high strength to withstand the stresses of pivoting from the folded to deployed positions and maintain the integrity of the wound closure device upon implantation. The fastener can slowly degrade so that the fastener is replaced with new tissue over time. Alternatively, hinge 131 may be a living hinge, such as a thin flexible web of a polymer, formed at the intersection of the elongate body 132 with the plug member 134. In other embodiments, a hinge may be formed through welding the plug member and the elongate body together.

The elongate body 132 and plug member 134 may transform from the folded position (for insertion) as depicted in FIG. 13A to a deployed state as depicted in FIG. 13C for positioning and placement within tissue. In embodiments, plug member 134 may be normally biased toward the folded position such that the plug member 134 is longitudinally aligned with the elongate body 132. Consequently, as the wound closure device 130 is placed within tissue and pulled in the direction of arrow "p" depicted in FIG. 13C, the plug member 134 pivots away from the elongate body 132 to be substantially perpendicular to the elongate body 132, the plug member 134 effectively acting as a flange to prevent pullout of the wound closure device 130 from tissue. Alternatively, wound closure devices may be positioned through use of an insertion device, which will be later described.

In the collapsed or folded position, as illustrated in FIG. 13A, the slim profile is preferentially used for insertion into tissue. Moreover, as shown in FIG. 13B, the plug member 134 includes rounded edges to provide an atraumatic tip for insertion. In the deployed state, as illustrated in FIGS. 13C and 13D, the width "w" of the plug member 134 may be based on the size of the incision, and the length "l" of the elongate body 132 may be made any length, such as longer than needed so as to be cut to length after insertion into tissue.

In some embodiments, the elongate body 132 may be fabricated from a material that encourages surrounding tissue of the wound to chemically bond thereto and to encourage cell growth and tissue proliferation. Moreover, the tissue facing surface 136 of the plug member 134 may include other polymer materials to encourage tissue integration. The distal surface 135 of the plug member 134 may include an anti-adhesive coating to prevent tissue adhesion.

Another embodiment of a wound closure device which is pivotably connected for insertion into a wound is shown in FIGS. 14A-14C. The wound closure device 140 includes an elongate body 142 and a plug member 144 formed from a pair of substantially identically shaped sections 144a and 144b. The elongate body 142 and the sections 144a and 144b of the plug member 144 are coupled via one or more hinges 141. Sections 144a and 144b of the plug member 144 are pivotably mounted on hinges 141 to move on a common pivot axis.

Shaped sections 144a and 144b are illustrated as generally triangular in geometry, although other geometries are envisioned, such as rectangular. Shaped sections 144a, 144b, each include an abutment surface 143a, and 143b, respectively (FIG. 14B). For insertion, abutment surfaces 143a, 143b are positioned generally parallel the elongate body 142. Once inserted and positioned, the abutment surfaces are approximated so as to dispose sections 144a and 144b generally perpendicular to the elongate body 142. The abutment surfaces 143a, 143b provide control as to how angled the shaped sections reside with respect to the elongate body 142. For example, if the abutment surfaces were angled greater than or less than 90° with respect to the elongate body (as opposed to generally perpendicular in FIG. 14B), the shaped sections 144a and 144b would similarly be disposed at an angle greater than or less than 90° with respect to the elongate body.

Prior to placement within tissue, sections 144a and 144b of the plug member may be folded up in the direction of arrow "b" depicted in FIG. 14B. As the wound closure device 140 is placed within tissue and pulled in the direction of arrow "p" depicted in FIG. 14C, sections 144a and 144b of the plug member 144 pivots away from the elongate body 142 (shown in phantom) to be substantially perpendicular to the elongate body 142, the plug member 144 effectively acting as a flange to prevent pullout of the wound closure device 140 from tissue. As illustrated, sections 144a and 144b are triangular in shape to prevent the plug member 144 from deploying beyond about 90 degrees from the elongate member 142 to prevent the inadvertent removal of the wound closure device 140 from the tissue. It is envisioned that sections 144a and 144b of the plug member 144 need not be substantially similar in shape.

In embodiments, the elongate body 142 may be a pre-formed hydrogel having an absorbable mesh layer. In embodiments, the pre-formed hydrogel may be formed from an 8 arm, 15 kDa PEG first precursor and a second precursor, such as collagen, gelatin, or other aminated biodegradable polymer, such as polysaccharides like aminated dextran or hyaluronic acid. In embodiments, the plug member 144 may be a pre-formed hydrogel which may or may not have an anti-adhesive coating on the distal end 145 thereof and a degradable or non-degradable mesh attached to the tissue facing surface 146.

A pre-formed hydrogel enables quick insertion and delivery of the wound closure device as there is no waiting period for the device to form in situ. Moreover, a pre-formed component avoids the possibility of components reacting with tissue other than the target wound and avoids spilling of material into the body cavity or elsewhere, such as on a skin surface. Methods for making pre-formed hydrogel include simultaneously spraying the first precursor and the second precursor into a mold of a desired geometry.

In embodiments, the elongate body and/or the plug member may include unreacted hydrogel which is embedded in the mesh or on which the mesh is attached, which can be solubilized and reacted within the tissue, thereby gelling within the mesh structure and binding the tissue thereto. This allows the mesh to bind to the interior wall of the tissue and prevents other components from working their way into the wound.

Alternatively, the wound closure device including a mesh may be first inserted into a wound and subsequently a hydrogel may be injected with a static mixer into the wound to fill the void and encase the mesh. In embodiments, the plug member may include a pre-formed hydrogel and the elongate body may be unreacted so that a hydrogel can be injected into the wound to hold the tissue and mesh in place.

Figure 15A:
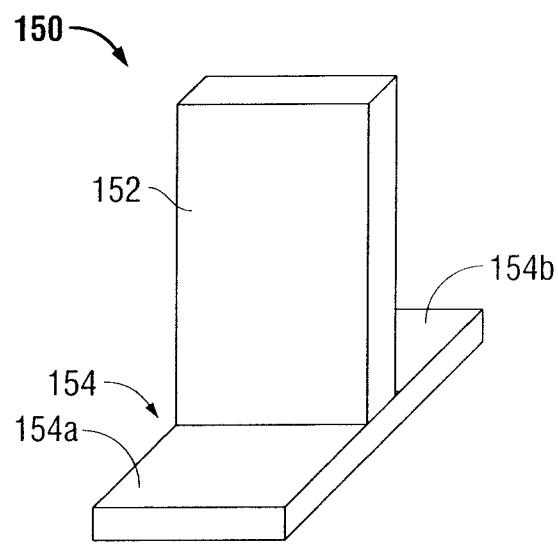
FIG. 15A is a perspective view of a wound closure device in a deployed position in accordance with another embodiment of the present disclosure.
Figure 15B:
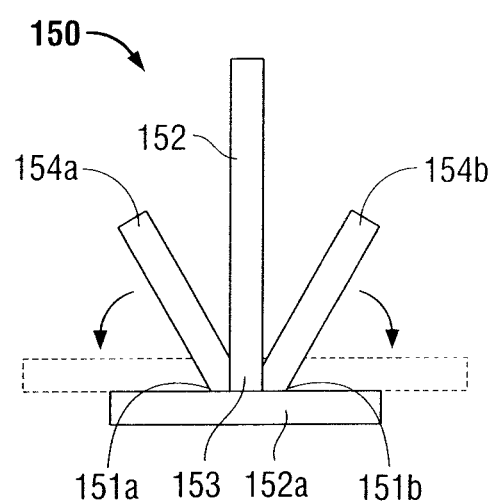
FIG. 15B is a side view of the wound closure device of FIG. 15A illustrated in a first, folded position with the second, deployed position shown in phantom.

Turning now to FIGS. 15A-15B, another embodiment of a wound closure device which includes an elongate body and plug member including a pair of shaped sections is shown. FIG. 15A illustrates wound closure device 150 in a deployed position having an elongate body 152 and a plug member 154 formed from a pair of substantially identically shaped sections 154a and 154b. Sections 154a and 154b of the plug member 154 are pivotably mounted on independent hinges 151a and 151b as illustrated in FIG. 15B. Sections 154a and 154b are shown pivoting away from the elongate body 152 to the deployed position of FIG. 15A (in phantom). Elongate body 152 includes a stop member 152a at distal end 153 to prevent sections 154a and 154b of plug member 154 from over extending beyond angle α, which is about 90 degrees.

Wound closure devices of the present disclosure may be inserted into a passageway of a cannula or other portal access device having a sleeve extending through the tissue wall into the cavity of the patient. The wound closure device is moved through the passageway of the sleeve until the plug member exits the sleeve into the cavity. The plug member may be positioned so that the tissue facing surface abuts the wound and the sleeve is removed leaving the elongate body disposed within the perforated tissue. Accordingly, the wound closure device must be sufficiently pliable to be placed within the access device, yet be resilient enough to support the tissue and seal the wound. Alternatively, the wound closure device may include mechanical means for ease of insertion and placement of the device.

In embodiments, additional methods of securing a wound closure device of the present disclosure to tissue may be utilized. For example, bandages, films, gauzes, tapes, felts, combinations thereof, and the like, may be combined therewith or applied over a wound closure device of the present disclosure, as well as tissue surrounding the device. Similarly, additional adhesives may be applied thereto; sutures may be utilized to affix the wound closure device to tissue, combinations thereof, and the like.

Bioactive agents may be added to the wound closure device to provide specific biological or therapeutic properties thereto. Any product which may enhance tissue repair, limit the risk of sepsis, and modulate the mechanical properties of the wound closure device may be added during the preparation of the device or may be coated on the device or into the pores of a mesh attached thereto.

Moreover, the wound closure device may also be used for delivery of one or more bioactive agents. The bioactive agents may be incorporated into the wound closure device during formation of the device, such as by free suspension, liposomal delivery, microspheres, etc., or by coating a surface of the wound closure device, or portion thereof, such as by polymer coating, dry coating, freeze drying, applying to a mesh surface, ionically, covalently, or affinity binding to functionalize the degradable components of the wound closure device. Thus, in some embodiments, at least one bioactive agent may be combined with a component of the wound closure device, i.e., the elongate body and/or plug member, during formation to provide release of the bioactive agent during degradation of the wound closure device. As the wound closure device degrades or hydrolyzes in situ, the bioactive agents are released. In other embodiments, bioactive agents may be coated onto a surface or a portion of a surface of the elongate body or plug member of the wound closure device for quick release of the bioactive agent.

A bioactive agent as used herein is used in the broadest sense and includes any substance or mixture of substances that have clinical use. Consequently, bioactive agents may or may not have pharmacological activity per se, e.g., a dye. Alternatively a bioactive agent could be any agent that provides a therapeutic or prophylactic effect; a compound that affects or participates in tissue growth, cell growth, and/or cell differentiation; an anti-adhesive compound; a compound that may be able to invoke a biological action such as an immune response; or could play any other role in one or more biological processes. A variety of bioactive agents may be incorporated into the mesh.

Examples of classes of bioactive agents, which may be utilized in accordance with the present disclosure include, for example, anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of bioactive agents may be used.

Other bioactive agents, which may be included as a bioactive agent include: local anesthetics; non-steroidal anti-fertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents, such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics, such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anticonvulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins and cytotoxic drugs; chemotherapeutics; estrogens; antibacterials; antibiotics; anti-fungals; anti-virals; anticoagulants; anticonvulsants; antidepressants; antihistamines; and immunological agents.

Other examples of suitable bioactive agents, which may be included in the wound closure device include, for example, viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons ($\beta$-IFN, $\alpha$-IFN and $\gamma$-IFN); erythropoietin; nucleases; tumor necrosis factor; colony stimulating factors (e.g., GCSF, GM-CSF, MCSF); insulin; anti-tumor agents and tumor suppressors; blood proteins, such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids, such as anti-sense molecules, DNA, RNA, RNAi; oligonucleotides; polynucleotides; and ribozymes.

In embodiments, the polymers forming the wound closure device, such as precursors and/or hydrogels formed from the precursors, may contain visualization agents to improve their visibility during surgical procedures. Visualization agents may be selected from a variety of non-toxic colored substances, such as dyes, suitable for use in implantable medical devices. Suitable dyes are within the purview of those skilled in the art and may include, for example, a dye for visualizing a thickness of the hydrogel as it is formed in situ, e.g., as described in U.S. Pat. No. 7,009,034. In some embodiments, a suitable dye may include, for example, FD&C Blue #1, FD&C Blue #2, FD&C Blue #3, FD&C Blue #6, D&C Green #6, methylene blue, indocyanine green, other colored dyes, and combinations thereof. It is envisioned that additional visualization agents may be used such as fluorescent compounds (e.g., flurescein or eosin), x-ray contrast agents (e.g., iodinated compounds), ultrasonic contrast agents, and MRI contrast agents (e.g., Gadolinium containing compounds).

The visualization agent may be present in any precursor component solution. The colored substance may or may not become incorporated into the resulting hydrogel. In embodiments, however, the visualization agent does not have a functional group capable of reacting with the precursor(s).

In embodiments, the bioactive agent may be encapsulated by polymers utilized to form the wound closure device. For example, the polymer may form microspheres around the bioactive agent.

Suitable bioactive agents may be combined with the wound plug either prior to or during the manufacturing process. Bioactive agents may be admixed or combined with polymers to yield a plug with bioactive properties. In other embodiments, the bioactive agent may be combined with the present disclosure for example, in the form of a coating, after the plug has been shaped. It is envisioned that the bioactive agent may be applied to the present disclosure in any suitable form of matter, e.g., films, powders, liquids, gels and the like.

It should be understood that various combinations of elongate bodies and plug members may be used to fabricate the wound closure device according to the present disclosure. For example, any of the elongate bodies of the embodiments described above may be combined with any of the plug members also described above, dependent upon the type of wound to be treated and the properties desired from the wound closure device.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments of the present disclosure. Various modifications and variations of the wound closure device, as well as methods of forming the elongate body and plug member of the wound closure device and attaching the components together, will be apparent to those skilled in the art from the foregoing detailed description. Such modifications and variations are intended to come within the scope and spirit of the claims appended hereto.

What is claimed is:

1. A wound closure device for repairing and sealing a perforation in tissue at a laparoscopic port site of the tissue, the wound closure device comprising:
    an elongate body that extends longitudinally between a proximal end and a distal end, the elongate body having a pair of planar side surfaces, the elongate body being adapted to be secured within the perforation at the laparoscopic port site;
    a plug member including a first section and a second section, each of the first and second sections being hingedly and directly connected to one of the pair of planar side surfaces of the elongate body, the first and second sections being independently movable relative to one another, the first and second sections being movable between a deployed position in which the first and second sections extend at a predetermined angle relative to the elongate body, and a collapsed position in which the first and second sections extend at an angle relative to the elongate body, the angle being less than the predetermined angle of the deployed position; and
    a stop member at the distal end of the elongate body configured to prevent the first and second sections of the plug member from extending beyond the predetermined angle of the deployed position.

2. The wound closure device of claim 1, wherein the first and second sections are identical.

3. The wound closure device of claim 1, wherein the first and second sections are pivotably mounted on independent hinges.

4. The wound closure device of claim 1, wherein the predetermined angle is 90°.

5. The wound closure device of claim 1, wherein an outer dimension of the plug member in the deployed position is greater than an outer dimension of the stop member.

6. The wound closure device of claim 5, wherein the outer dimension of the plug member in the collapsed position is equal to or smaller than the outer dimension of the stop member.

7. The wound closure device of claim 1, wherein the elongate body, the plug member, or both, includes at least one reactive group that bonds to tissue.

8. The wound closure device of claim 1, wherein the elongate body, the plug member, or both, includes at least one of a hydrogel, a mesh, or a foam.

9. The wound closure device of claim 1, wherein each of the first and second sections of the plug member is adapted to move independent of the stop member.

10. The wound closure device of claim 1, wherein the stop member is dimensioned to remain axially stationary as the first and second sections of the plug member move between the deployed position and the collapsed position.

11. The wound closure device of claim 1, wherein the first and second sections of the plug member are longitudinally aligned with each other and longitudinally offset from the stop member.

12. The wound closure device of claim 1, wherein each of the first and second sections are independently movable relative to one another such that a first one of the first and second sections is positionable within the collapsed position while a second one of the first and second sections is positionable within the deployed position, wherein the predetermined angle is at a maximum in the deployed position such that the second one of the first and second sections is fully deployed.

13. The wound closure device of claim 1, wherein the first and second sections are separate and distinct from one another.

14. A wound closure device for repairing and sealing a perforation in tissue at a laparoscopic port site of the tissue, the wound closure device comprising:
    an elongate body defining a longitudinal axis, the elongate body including a stop member disposed at a distal end thereof and at least one planar side surface; and
    a plug member adapted to be secured to the tissue at the laparoscopic port site adjacent to the perforation, the plug member including a tissue facing surface, the plug member pivotable to a deployed position in which the tissue facing surface is transverse to the longitudinal axis of the elongate body, the plug member including at least two sections, at least one of the at least two sections being hingedly and directly connected to the at least one planar side surface of the elongate body, the at least two sections being independently pivotable relative to one another,
    wherein the stop member maintains the plug member in the deployed position.

15. The wound closure device of claim 14, wherein each of the at least two sections is independently hingedly connected to the elongated body and independently pivotable relative to the elongated body.

16. The wound closure device of claim 15, wherein the at least two sections are identical.

17. The wound closure device of claim 14, wherein an outer dimension of the plug member in the deployed position is greater than an outer dimension of the stop member.

18. The wound closure device of claim 14, wherein the elongate body, the plug member, or both, includes at least one reactive group that bonds to tissue.

19. The wound closure device of claim 14, wherein the elongate body, the plug member, or both, includes at least one of a hydrogel, a mesh, or a foam.

20. The wound closure device of claim 14, wherein the stop member is dimensioned to remain axially stationary as the plug member pivots to the deployed position.

21. The wound closure device of claim 14, wherein the stop member is dimensioned to prevent the plug member from over extending beyond the deployed position.

22. A wound closure device for repairing and sealing a perforation in tissue at a laparoscopic port site of the tissue, the wound closure device comprising:
an elongate body that extends longitudinally between a proximal end and a distal end, the elongate body having a pair of planar side surfaces, the elongate body being adapted to be secured within the perforation at the laparoscopic port site;
a plug member adapted to be secured to the tissue at the laparoscopic port site adjacent to the perforation, the plug including a first section and a second section, each of the first and second sections being hingedly and directly connected to one of the pair of planar side surfaces of the elongate body, the first and second sections being independently movable relative to one another, the first and second sections being movable between a deployed position in which the first and second sections extend at a predetermined angle relative to the elongate body, and a collapsed position in which the first and second sections extend at an angle relative to the elongate body, the angle being less than the predetermined angle of the deployed position; and
a stop member at the distal end of the elongate body adapted to prevent the first and second sections of the plug member from extending beyond the predetermined angle of the deployed position, the stop member adapted to support the plug member in the deployed position adjacent to the laparoscopic port site to enable repair and sealing of the perforation at the laparoscopic port site.

* * * * *